United States Patent
Baraso et al.

(10) Patent No.: US 8,206,306 B2
(45) Date of Patent: Jun. 26, 2012

(54) ULTRASOUND SYSTEMS AND METHODS FOR ORTHOPEDIC APPLICATIONS

(75) Inventors: Randall R. Baraso, Mount Pleasant, SC (US); Bruce M. Frankel, Mount Pleasant, SC (US); Kazutoshi Tsuchida, Tokyo (JP); Hiroaki Wakabayashi, Tokyo (JP)

(73) Assignee: Hitachi Aloka Medical, Ltd., Wallingford, CT (US)

( * ) Notice: Subject to any disclaimer, the term of this patent is extended or adjusted under 35 U.S.C. 154(b) by 0 days.

(21) Appl. No.: 12/917,721

(22) Filed: Nov. 2, 2010

(65) Prior Publication Data

US 2011/0208062 A1 Aug. 25, 2011

Related U.S. Application Data

(63) Continuation-in-part of application No. 12/775,047, filed on May 6, 2010.

(60) Provisional application No. 61/176,373, filed on May 7, 2009.

(51) Int. Cl.
*A61B 8/14* (2006.01)

(52) U.S. Cl. .................... 600/459; 600/462

(58) Field of Classification Search ........... 600/437–467
See application file for complete search history.

(56) References Cited

U.S. PATENT DOCUMENTS

| | | |
|---|---|---|
| 3,938,502 A | 2/1976 | Bom |
| 3,942,530 A | 3/1976 | Northeved |
| 4,273,111 A | 6/1981 | Tsukaya |
| 4,462,408 A | 7/1984 | Silverstein et al. |
| 4,489,727 A | 12/1984 | Matsuo et al. |
| 4,582,067 A | 4/1986 | Silverstein et al. |
| 4,756,313 A | 7/1988 | Terwilliger |
| 4,951,677 A | 8/1990 | Crowley et al. |
| 5,070,879 A | 12/1991 | Herres |
| 5,088,500 A | 2/1992 | Wedel et al. |
| 5,090,414 A | 2/1992 | Takano |
| 5,196,015 A | 3/1993 | Neubardt |
| 5,275,166 A | 1/1994 | Vaitekunas et al. |
| 5,325,860 A | 7/1994 | Seward et al. |
| 5,345,940 A | 9/1994 | Seward et al. |

(Continued)

FOREIGN PATENT DOCUMENTS

DE 102005047527 4/2007

(Continued)

OTHER PUBLICATIONS

PCT International Search Report and Written opinion dated Feb. 8, 2012.

(Continued)

*Primary Examiner* — Sanjay Cattungal
(74) *Attorney, Agent, or Firm* — McCarter & English, LLP

(57) ABSTRACT

Medical diagnostic instruments/systems are provided that include (i) a proximal handle configured and dimensioned to permit an operator to manually grasp the instrument; (ii) an ultrasound probe including a longitudinal shaft extending distally from the handle and terminating in a distal end, and an ultrasound transducer mounted with respect to the longitudinal shaft, the ultrasound transducer including an array of ultrasonic energy generation elements (iii) a tactile feeler probe mounted with respect to the ultrasound probe; and (iv) at least one hollow receiver member mounted with respect to the longitudinal shaft of the ultrasound probe, the at least one hollow receiver member configured to receive a K-wire to permit the instrument to be slidably mounted thereto for purposes of guiding the ultrasound and tactile feeler probes axially relative to a desired anatomical location. Advantageous methods for use of the disclosed instruments/systems are also provided.

22 Claims, 37 Drawing Sheets

U.S. PATENT DOCUMENTS

| | | | |
|---|---|---|---|
| 5,372,138 A | 12/1994 | Crowley et al. |
| 5,413,107 A | 5/1995 | Oakley et al. |
| 5,421,338 A | 6/1995 | Crowley et al. |
| 5,429,136 A | 7/1995 | Milo et al. |
| 5,474,558 A | 12/1995 | Neubardt |
| 5,499,630 A | 3/1996 | Hiki et al. |
| 5,512,034 A | 4/1996 | Finn et al. |
| 5,524,630 A | 6/1996 | Crowley |
| 5,588,432 A | 12/1996 | Crowley |
| 5,680,863 A | 10/1997 | Hossack et al. |
| 5,697,897 A | 12/1997 | Buchholtz et al. |
| 5,704,361 A | 1/1998 | Seward et al. |
| 5,713,363 A | 2/1998 | Seward et al. |
| 5,715,825 A | 2/1998 | Crowley |
| 5,735,792 A | 4/1998 | Vanden Hoek et al. |
| 5,752,517 A | 5/1998 | Harman et al. |
| 5,840,031 A | 11/1998 | Crowley |
| 5,846,204 A | 12/1998 | Solomon |
| 5,846,205 A | 12/1998 | Curley et al. |
| 6,004,269 A | 12/1999 | Crowley et al. |
| 6,036,649 A | 3/2000 | Yuasa |
| 6,039,693 A | 3/2000 | Seward et al. |
| 6,045,508 A | 4/2000 | Hossack et al. |
| 6,059,731 A | 5/2000 | Seward et al. |
| 6,099,475 A | 8/2000 | Seward et al. |
| 6,109,270 A | 8/2000 | Mah et al. |
| 6,129,672 A | 10/2000 | Seward |
| 6,149,599 A | 11/2000 | Schlesinger et al. |
| 6,165,127 A | 12/2000 | Crowley |
| 6,171,247 B1 | 1/2001 | Seward |
| 6,190,353 B1 | 2/2001 | Makower et al. |
| 6,224,552 B1 | 5/2001 | Jago et al. |
| 6,241,667 B1 | 6/2001 | Vetter et al. |
| 6,299,580 B1 | 10/2001 | Asafusa |
| 6,302,875 B1 | 10/2001 | Makower et al. |
| 6,306,096 B1 | 10/2001 | Seward |
| 6,306,097 B1 | 10/2001 | Park et al. |
| 6,364,840 B1 | 4/2002 | Crowley |
| 6,398,736 B1 | 6/2002 | Seward |
| 6,413,215 B1 | 7/2002 | Wu et al. |
| 6,432,058 B1 | 8/2002 | Sloth |
| 6,438,413 B1 | 8/2002 | Taheri |
| 6,464,645 B1 | 10/2002 | Park et al. |
| 6,544,187 B2 | 4/2003 | Seward |
| 6,556,695 B1 | 4/2003 | Packer et al. |
| 6,572,553 B2 | 6/2003 | Crowley |
| 6,579,244 B2 | 6/2003 | Goodwin |
| 6,585,655 B2 | 7/2003 | Crowley |
| 6,592,520 B1 | 7/2003 | Peszynski et al. |
| 6,655,386 B1 | 12/2003 | Makower et al. |
| 6,656,136 B1 | 12/2003 | Weng et al. |
| 6,719,692 B2 | 4/2004 | Kleffner et al. |
| 6,746,402 B2 | 6/2004 | Ustuner |
| 6,796,985 B2 | 9/2004 | Bolger et al. |
| 6,849,047 B2 | 2/2005 | Goodwin |
| 7,037,271 B2 | 5/2006 | Crowley |
| 7,059,330 B1 | 6/2006 | Makower et al. |
| 7,134,438 B2 | 11/2006 | Makower et al. |
| 7,156,812 B2 | 1/2007 | Seward et al. |
| 7,211,055 B2 | 5/2007 | Diederich et al. |
| 7,258,668 B2 | 8/2007 | Hirooka et al. |
| 7,297,115 B2 | 11/2007 | Bates et al. |
| 7,493,703 B2 | 2/2009 | Kim et al. |
| 7,503,895 B2 | 3/2009 | Rabiner et al. |
| 2001/0031924 A1 | 10/2001 | Seward |
| 2002/0120192 A1 | 8/2002 | Nolte et al. |
| 2003/0013936 A1 | 1/2003 | Jackson |
| 2003/0176807 A1 | 9/2003 | Goetz et al. |
| 2003/0205029 A1 | 11/2003 | Chapolini et al. |
| 2003/0225331 A1 | 12/2003 | Diederich et al. |
| 2005/0101866 A1 | 5/2005 | Goodwin |
| 2005/0182324 A1 | 8/2005 | Angelsen et al. |
| 2005/0203396 A1 | 9/2005 | Angelsen et al. |
| 2005/0203416 A1 | 9/2005 | Angelsen et al. |
| 2006/0173307 A1 | 8/2006 | Amara et al. |
| 2006/0178594 A1 | 8/2006 | Neubardt et al. |
| 2006/0235299 A1 | 10/2006 | Martinelli |
| 2006/0276721 A1 | 12/2006 | McGinnis |
| 2007/0167821 A1 | 7/2007 | Lee et al. |
| 2007/0167823 A1 | 7/2007 | Lee et al. |
| 2007/0249939 A1 | 10/2007 | Gerbi et al. |
| 2008/0146918 A1 | 6/2008 | Magnin et al. |
| 2008/0146926 A1 | 6/2008 | Stauch et al. |
| 2008/0228231 A1 | 9/2008 | Raphael et al. |
| 2009/0099605 A1 | 4/2009 | Fallin et al. |
| 2011/0077525 A1 | 3/2011 | Baraso et al. |

FOREIGN PATENT DOCUMENTS

| | | |
|---|---|---|
| WO | WO 95/19143 | 7/1995 |
| WO | WO 2007/039036 | 4/2007 |
| WO | WO 2010/129773 A1 | 11/2010 |

OTHER PUBLICATIONS

Maguire et al., Evaluation of Intrapedicular Screw Position Using Intraoperative Evoked Electromyography, Spine, 20(9), p. 1068-1074, 1995.

Yongjung, Kim J. et al., Thoracic pedicle screw placement: Free-hand technique, Neurology India, vol. 53, No. 4, p. 512-510, 2005.

Kantelhardt, Sven R. et al., Intraosseous Ultrasound in the Placement of Pedicle Screws in the Lumbar Spine, Spine, vol. 34, No. 4, p. 400-407, 2009.

Kantelhardt, Sven R. et al., Intra-osseous ultrasound for pedicle screw positioning in the subaxial cervical spine: an experimental study, Acta Neurochir, DOI 10.1007/s00701-009-0447-6, 2009.

The Laguna pedicle Screw System Surgical Technique Guide, Pedicle Preparation, Allez Spine, Doc. 56003_B, p. 9, 2009, available at http://www.allezspine.com/pdfs/56003_C_Laguna_Surgical_Technique_Guide.pdf.

Minimally Invasive Spine Surgery, Taiwan Spine Center, 2009, available at http://www.taiwanspinecenter.com/tsc_e/sur_treatment/minimally_invasive.htm.

Pedicle Screw Stimulator, Consolidated Neuro Supply, 2009, available at http://www.neurosupply.com/subdermal_needles.htm.

Spine Navigation Software, Stryker, 2009, available at http://www.stryker.corn/en-us/products/Spine/SpineNavigationSurgery/index.htm.

Smart Instrumentation for Spine Navigation Surgery, Stryker, 2009, available at http://www.stryker.com/en-us/products/Spine/SpineNavigationSurgery/006198.

Spinal Navigation & 3-D Imaging: Giving Doctors and Patients the Whole Picture, Sky Ridge Medical Center, p. 18-19, 2009, available at http://www.skyridge.ehc.com/CPM/Health%20and%20Wellness%20Spine%20Choi%2Oreduced.pdf.

Peterson, Devin, Idiopathic Scoliosis, McMaster University, 2010, available at fhs.mcmaster.ca/surgery/documents/idiopathic_scoliosis.pdf.

PCT International Search Report and Written Opinion dated Jul. 19, 2010.

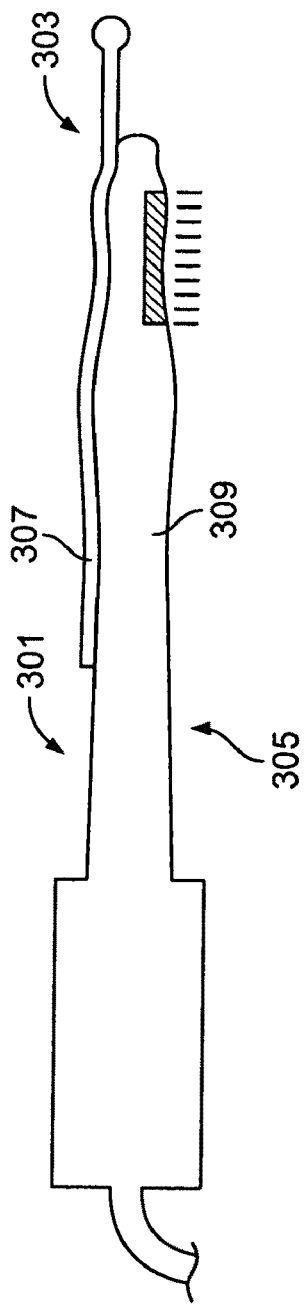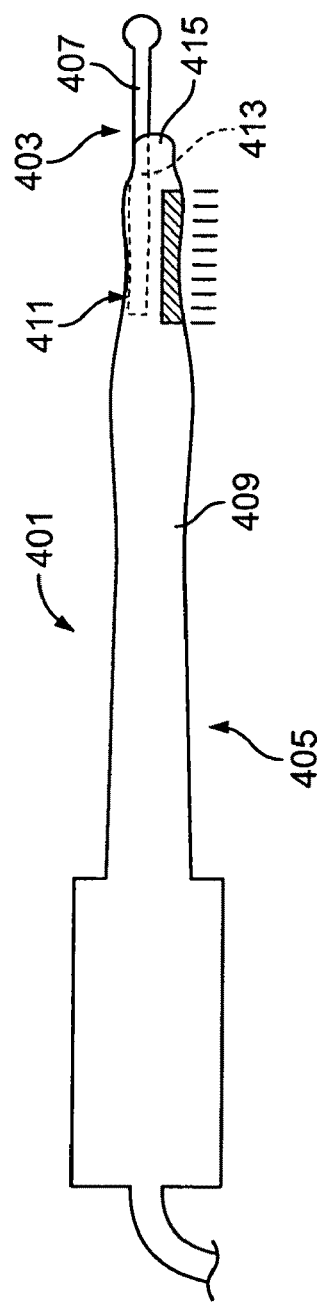
FIG. 3
FIG. 4

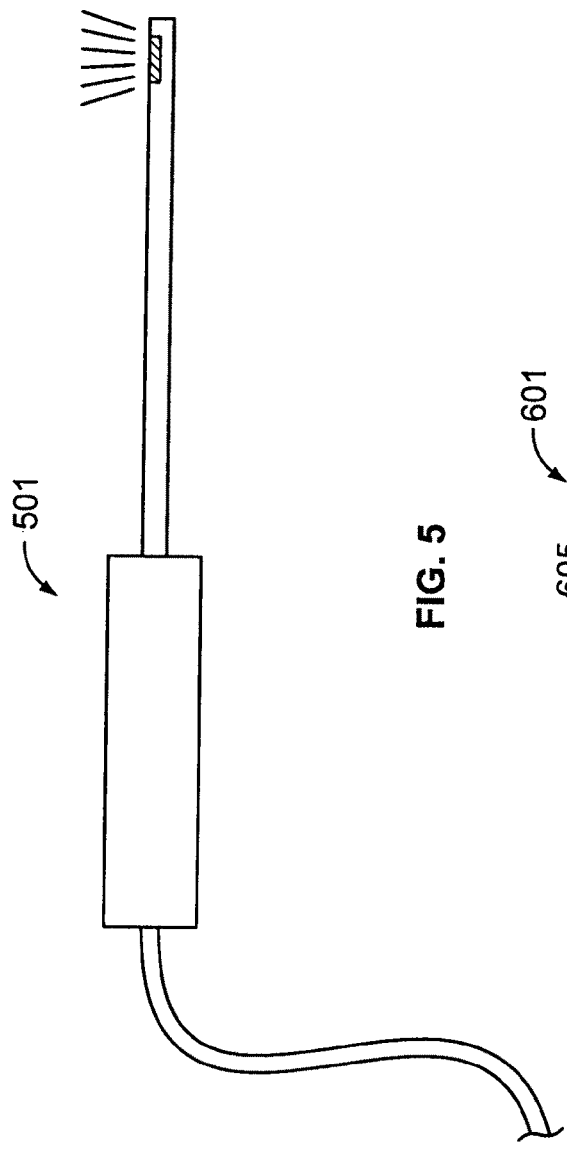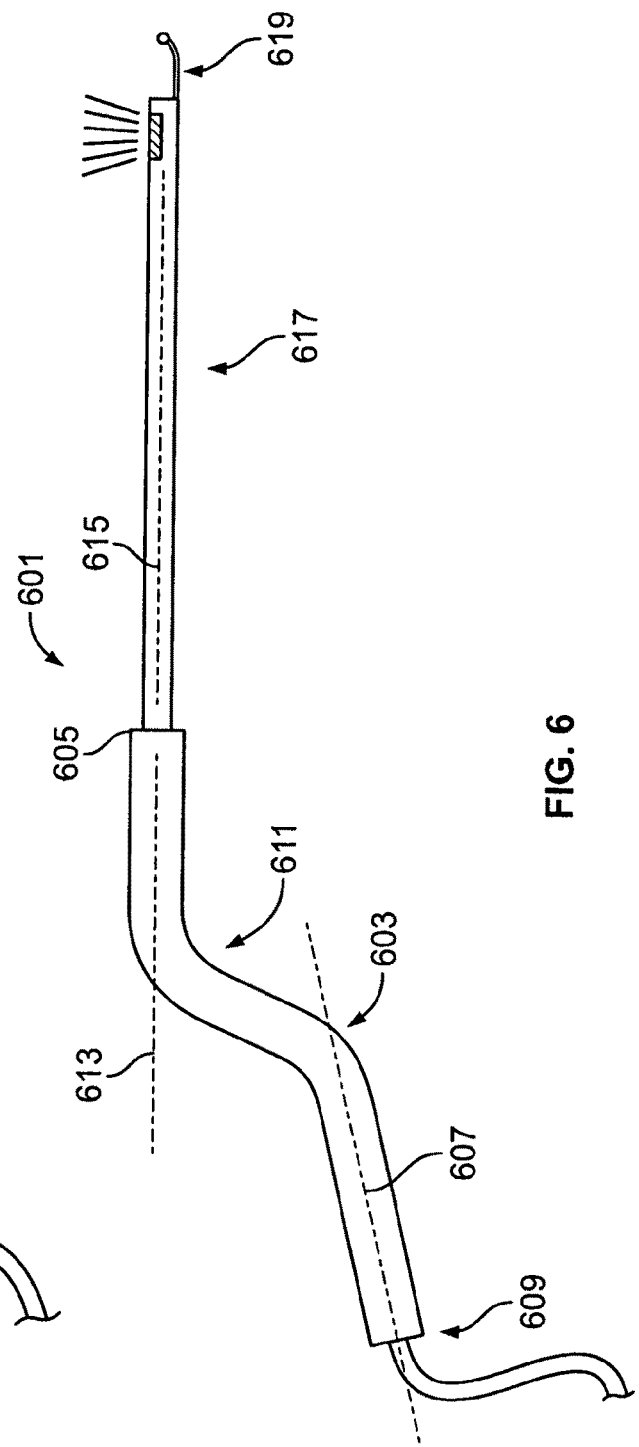

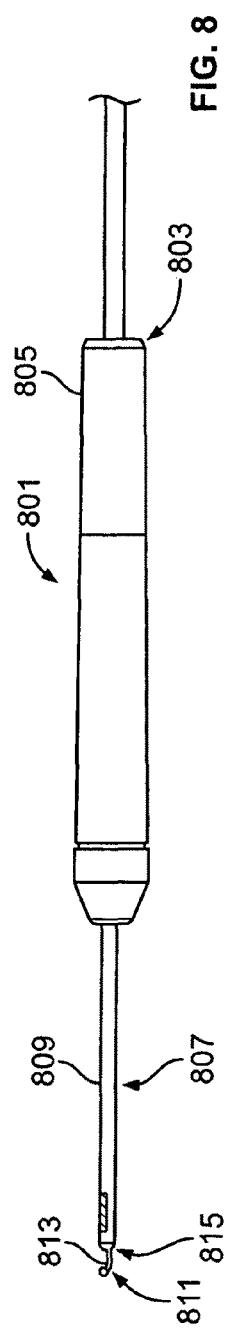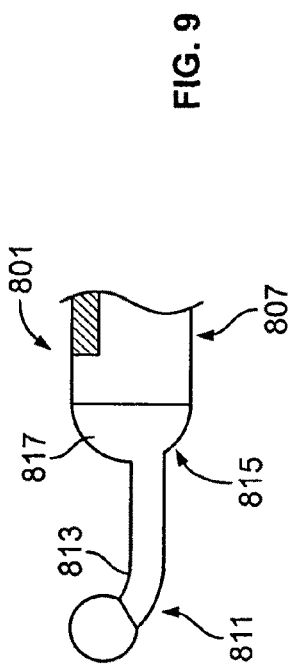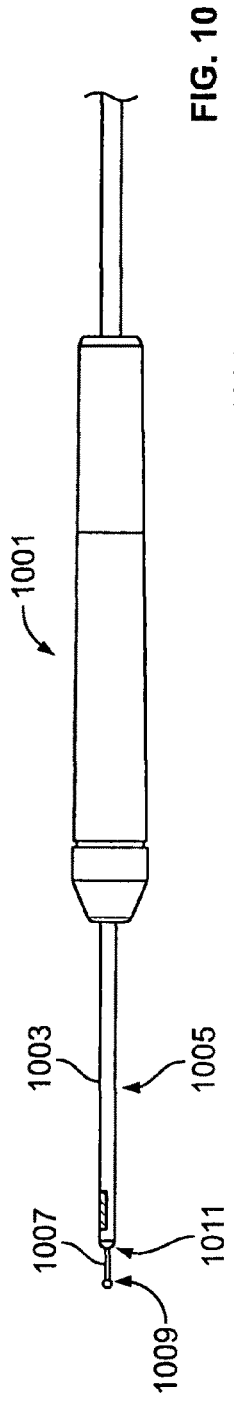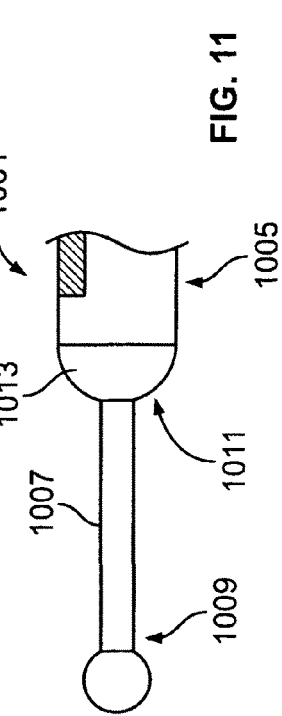

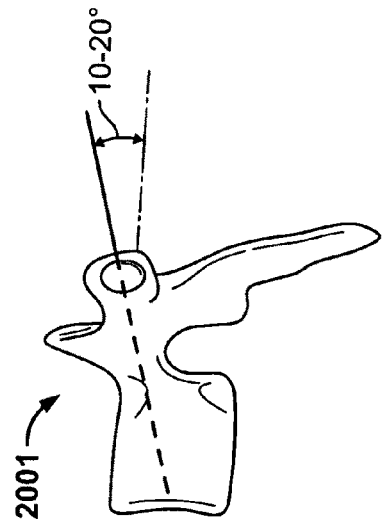
FIG. 22
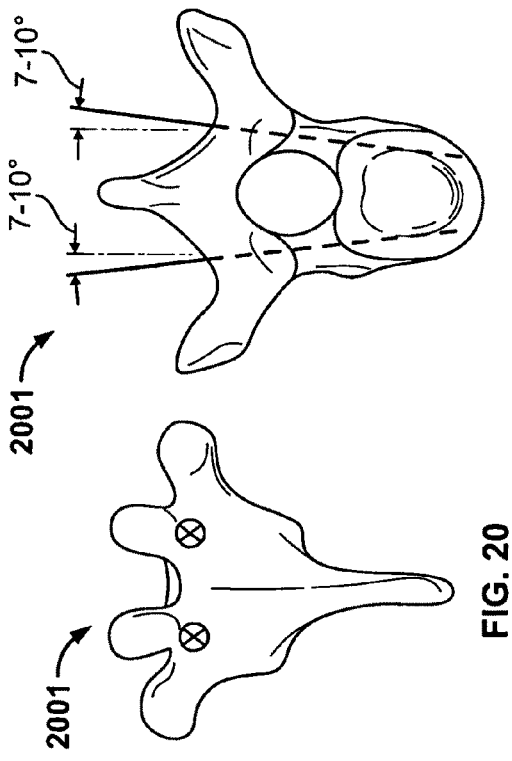
FIG. 20
FIG. 21
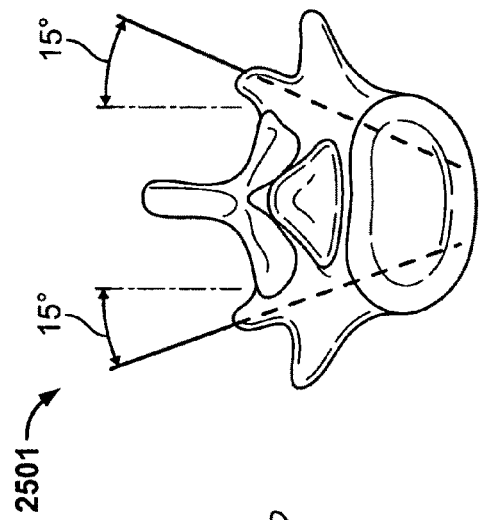
FIG. 25
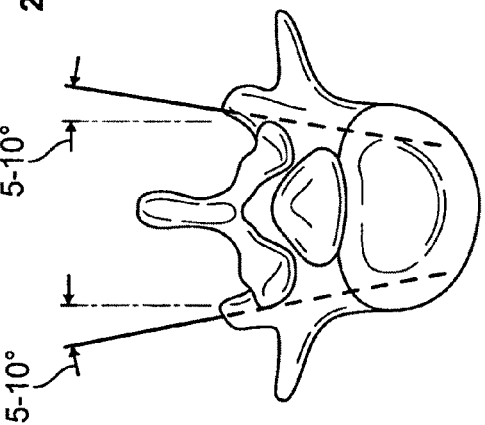
FIG. 24
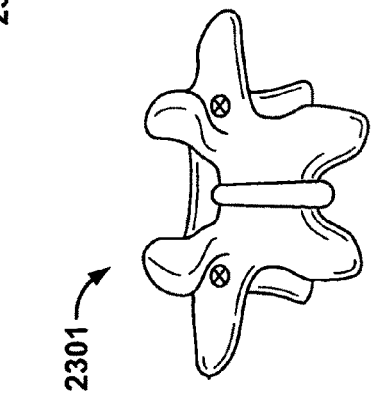
FIG. 23

L 2/3 Listhesis

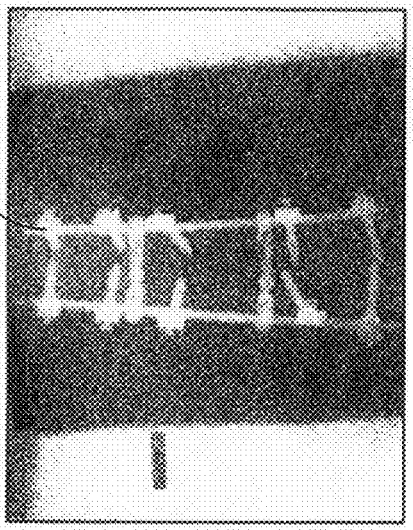
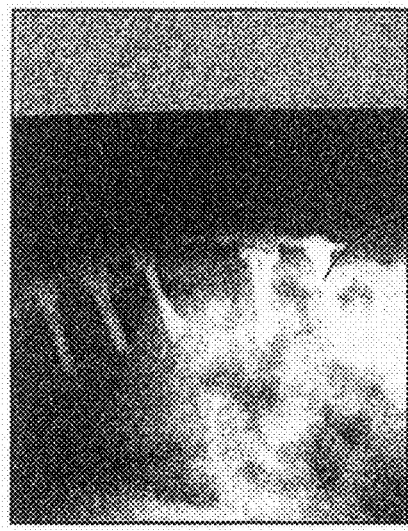
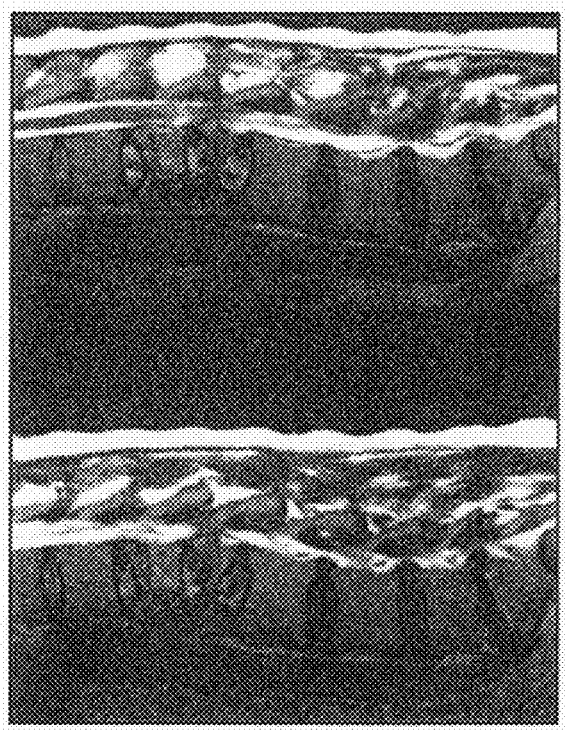

Progressive Kyphosis
Pain
Paraparesis

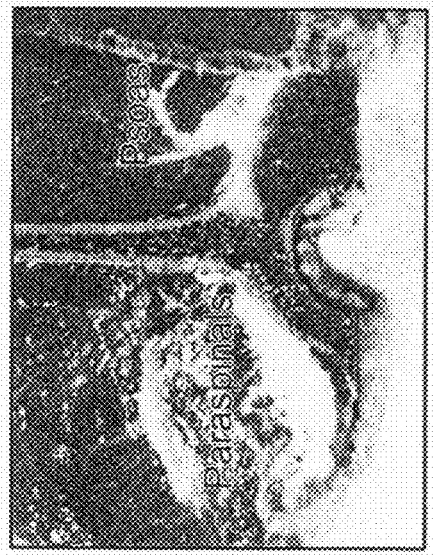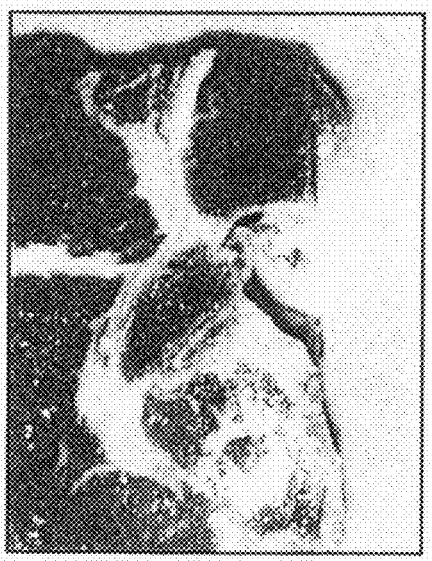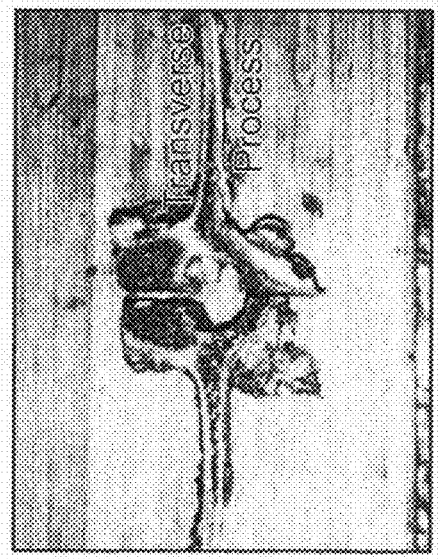
FIG. 42

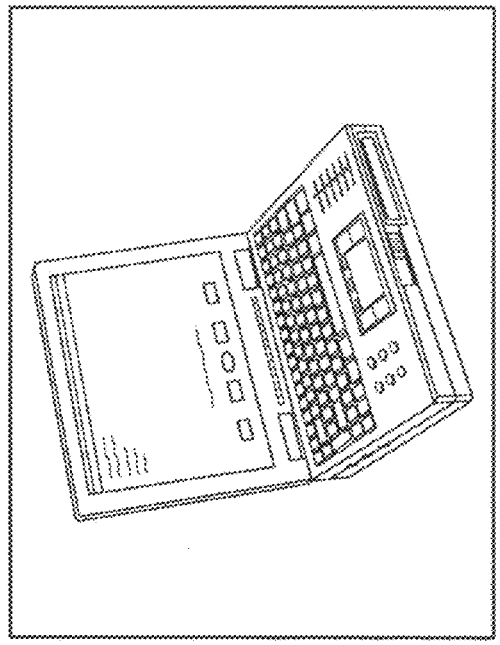
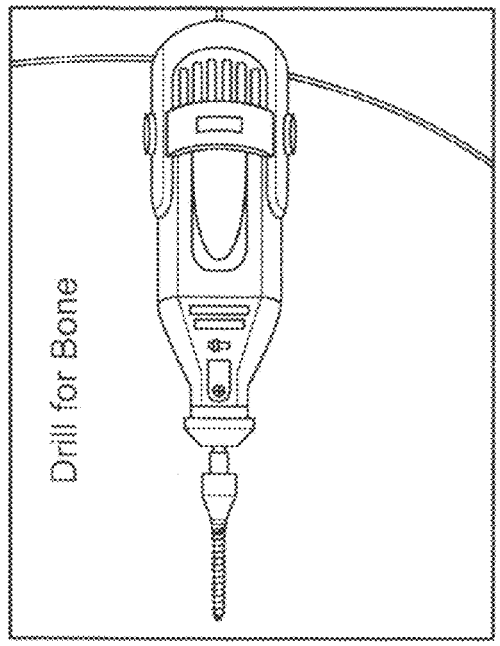
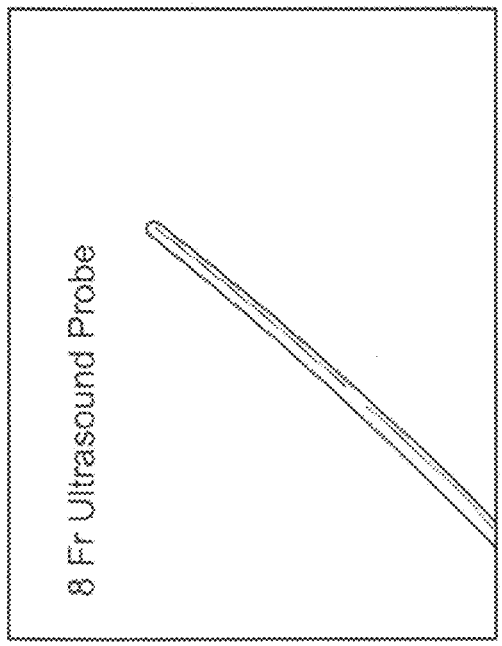
FIG. 44

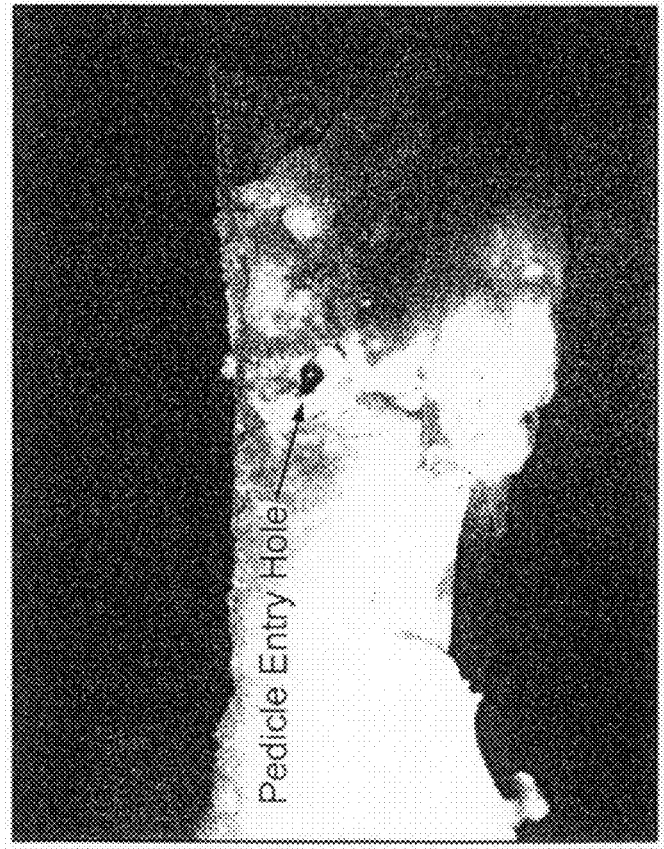
FIG. 46

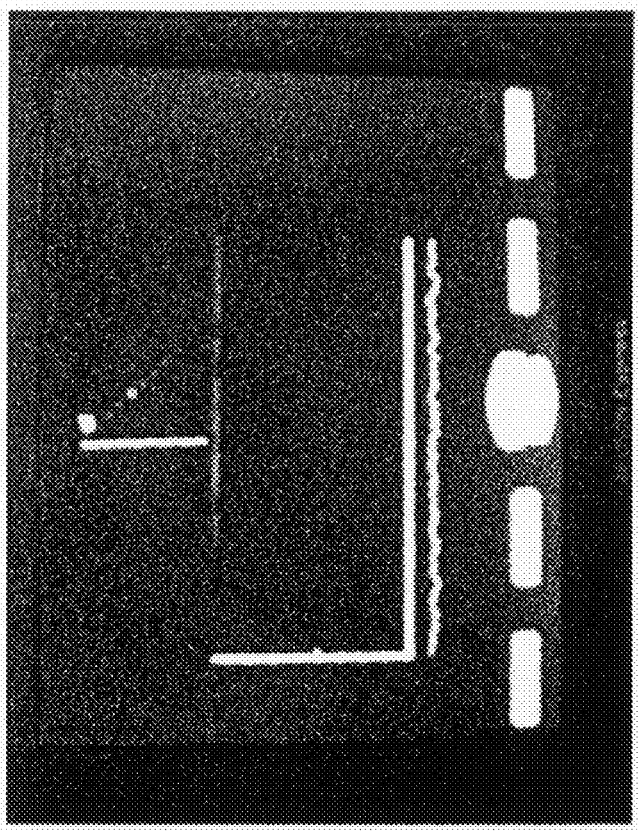
FIG. 48

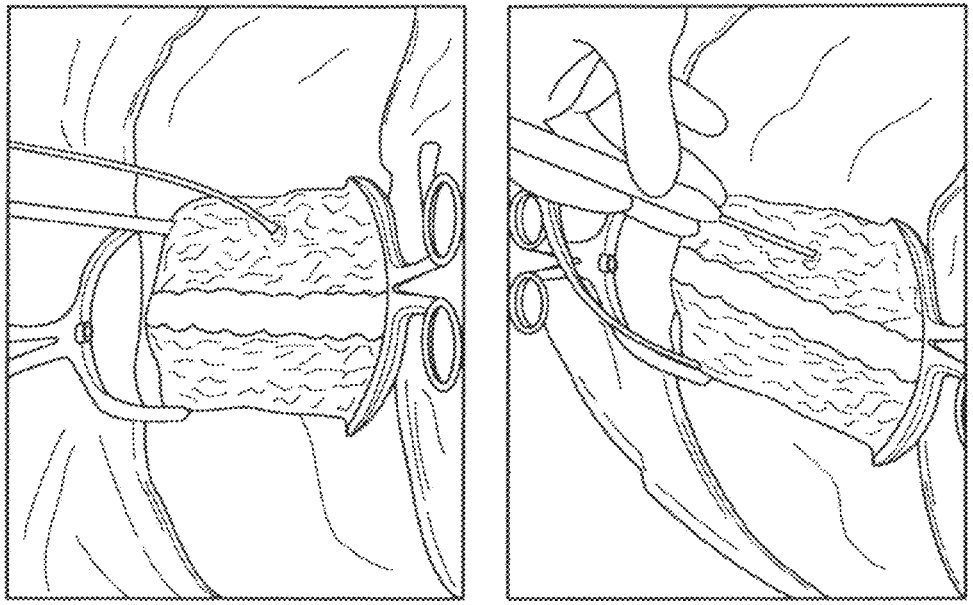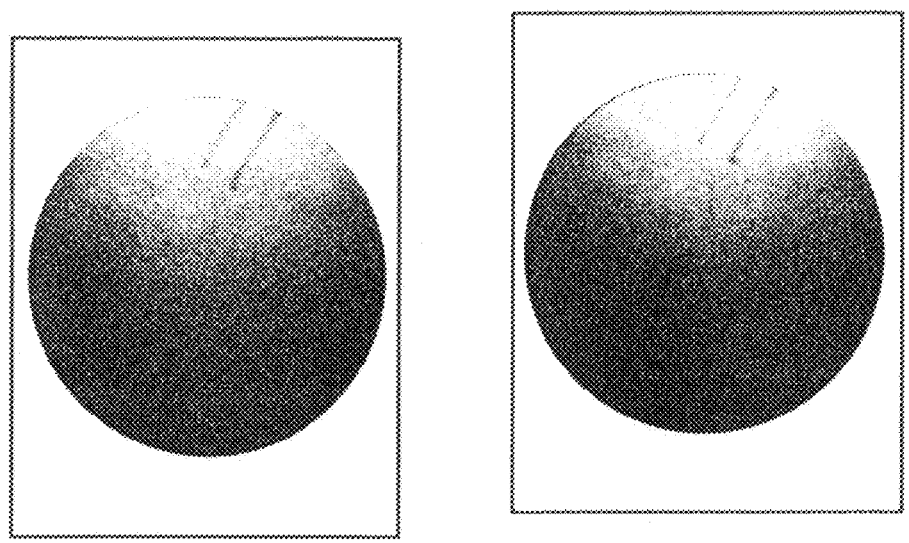
FIG. 54
Data Collected and Compared for Metal Pedicle Feeler (top) vs. Pedicle Ultrasound (Bottom)

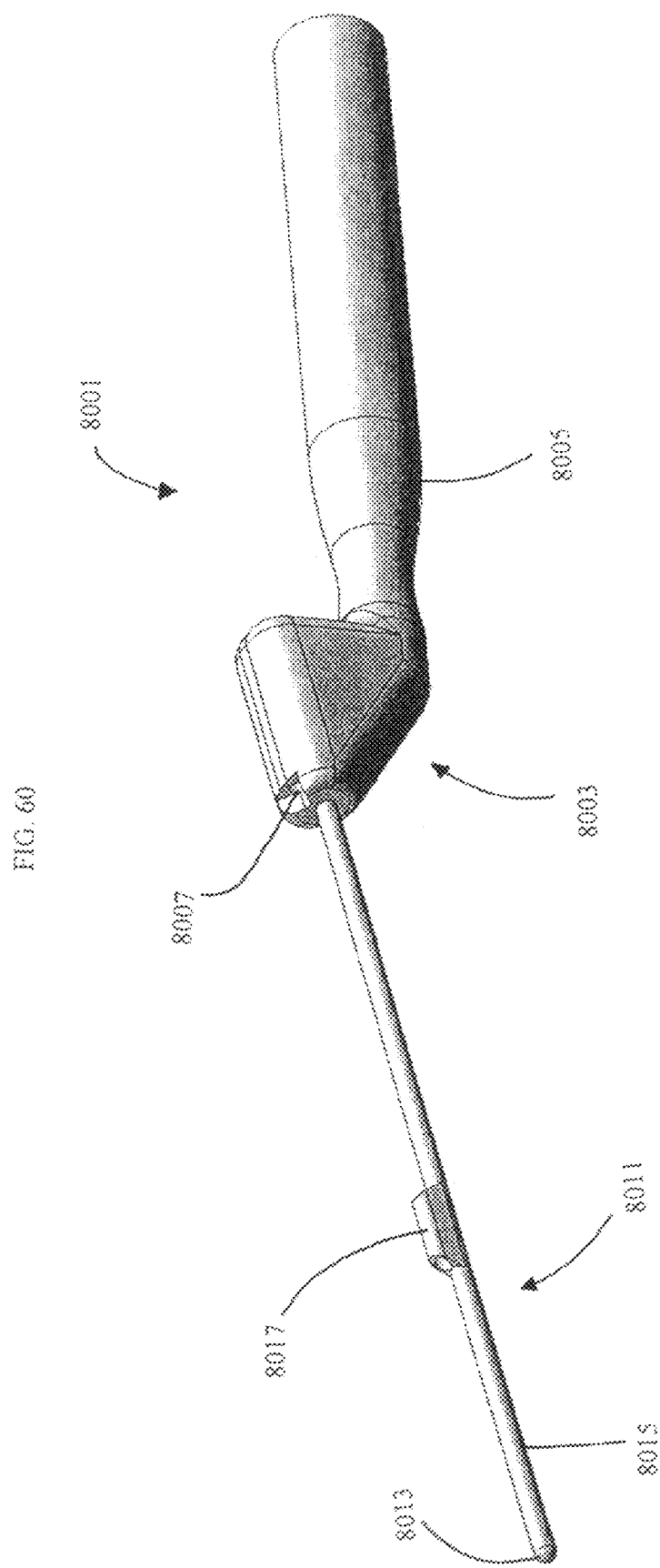

ULTRASOUND SYSTEMS AND METHODS FOR ORTHOPEDIC APPLICATIONS

CROSS-REFERENCE TO RELATED APPLICATIONS

This application claims priority to and is a continuation-in-part of co-pending U.S. patent application Ser. No. 12/775, 047 (entitled "Ultrasound Systems And Methods For Orthopedic Applications") filed May 6, 2010, which claims priority to Provisional App. Ser. No. 61/176,373 (entitled "Ultrasound for Orthopedic Application") filed May 7, 2009, both of which being hereby incorporated by reference in their entireties.

BACKGROUND

1. Technical Field

The present disclosure relates generally to equipment and procedures in the field of spinal surgery and, in exemplary implementations, to instruments, systems and methods for positioning and/or evaluating the positioning of pedicle screws in connection with orthopedic applications.

2. Background Art

Surgical techniques for spinal fixation vary widely in terms of the types of surgical equipment used, but modern surgical practice continues to rely quite heavily on the strength and stability afforded by the common pedicle screw. However, care must be taken during pedicle screw placement to protect against nerve damage. For example, after forming a pilot hole in the bone tissue of a pedicle but before moving forward with pedicle screw implantation, surgeons will typically take the opportunity to inspect the axially-extending side walls of the pilot hole to locate defects. With the advent and increasing use of minimally invasive surgical procedures that afford only a limited view with respect to anatomical structure, the risk of misplaced pedicle screws has increased. In the event a surgeon locates a breach of any significant size of the cortical bone adjacent the spinal column, he or she will mostly likely elect to redirect the screw to avoid the risk of complications such as pain, paralysis and hemorrhaging.

One method for locating such cortical breaches in regular use by surgeons is tissue palpation by means of the common tactile feeler probe. While surgeons are aware that this method has its limitations, including with regard to sensitivity in the case of relatively small breaches, as well as with regard to false positives, many if not most have become comfortable with the use of the tactile feeler probe. To the extent techniques and tools can be developed to facilitate continued effective use of tactile diagnostic techniques in the context of minimally invasive spinal surgical procedures, there is likely to be a strong market for same among current practitioners.

Recent developments in the use of ultrasound technology in surgical applications have shown promise. With the increasing miniaturization of electronics generally has come the ability to position ultrasound transducers to beneficial effect in increasingly smaller and, at least up until recently, harder to reach anatomical locations. Nevertheless, and despite efforts to date, a need remains for convenient, sanitary, low-cost, and effective equipment and related techniques for locating pilot hole bone tissue defects prior to pedicle screw implantation.

These and other needs are satisfied by the instruments, systems and methods disclosed herein, as will be apparent from the detailed description which follows, particularly when read in conjunction with the figures appended hereto.

SUMMARY

The present disclosure provides advantageous instruments, systems and methods for obtaining and/or determining anatomical information, e.g., locating pilot hole bone tissue defects prior to pedicle screw implantation.

In exemplary embodiments, a medical diagnostic instrument is provided that includes: (i) a proximal handle configured and dimensioned to permit an operator to manually grasp the instrument; (ii) an ultrasound probe including a longitudinal shaft extending distally from the handle and terminating in a distal end, and an ultrasound transducer mounted with respect to the longitudinal shaft, the ultrasound transducer including an array of ultrasonic energy generation elements (iii) a tactile feeler probe mounted with respect to the ultrasound probe; and (iv) at least one hollow receiver member mounted with respect to the longitudinal shaft of the ultrasound probe, wherein the at least one hollow receiver member is configured and dimensioned to receive a K-wire to permit the instrument to be slidably mounted thereto for purposes of guiding the ultrasound and tactile feeler probes axially relative to a desired anatomical location.

The ultrasound transducer and the distal end are generally cooperatively configured, oriented, and dimensioned to permit the operator to insert the ultrasound transducer and the distal end into a desired anatomical location to permit the operator to obtain thereat a corresponding two-dimensional image of the anatomical location for visual inspection by the operator for purposes of detecting ultrasonically-detectable anatomical properties. The array of ultrasonic energy generation elements may be side-firing and may be oriented in a linear array or a phased array. In addition, a feeler probe tip and a longitudinal shaft of the tactile feeler probe are generally cooperatively configured and dimensioned to permit the operator to insert the feeler probe tip and the longitudinal shaft of the tactile feeler probe into the desired anatomical location to permit the operator to perform thereat a tactile inspection of the selected anatomical location.

The disclosed medical diagnostic instrument may be advantageously employed in connection with a pedicle screw pilot hole formed in the spine of the human patient. In addition, the array of ultrasonic energy generation elements of the ultrasound transducer may extend axially along, and be positioned against, a selected portion of a side wall of the pedicle screw pilot hole. The feeler probe tip may be positioned against the selected portion of the side wall of the pedicle screw pilot hole. The medical diagnostic instrument may also include at least one channel in or adjacent to the handle of the instrument, the channel configured and dimensioned to receive the K-wire to permit the instrument to be slidably mounted thereto for purposes of guiding the ultrasound and tactile feeler probes axially relative to the desired anatomical location. Thus, the channel may be in the handle and extend therethrough, and/or be formed in an extension of the handle and extend therepast. The handle and the longitudinal shaft of the ultrasound probe may be of unitary construction or the ultrasound probe may be mounted with respect to the handle such that the longitudinal shaft of the ultrasound probe is supported, cantilever-style, by the handle housing. In addition, the tactile feeler probe may be mounted with respect to the ultrasound probe such that the longitudinal shaft of the tactile feeler probe is supported, cantilever-style, by the longitudinal shaft of the ultrasound probe.

The disclosed medical diagnostic instrument is typically adapted to cooperate with a cable assembly for carrying electrical signals to and from the ultrasound transducer in accordance with an ultrasonic imaging mode of use of the instrument. The cable assembly generally includes a proximal end including an electrical connector for connecting the instrument to a corresponding ultrasound console and current carrying wires extending distally from the electrical connector to the ultrasound transducer at least partially via a corresponding interior conduit formed in and extending longitudinally along the longitudinal shaft of the ultrasound probe. The current carrying wires also generally extend to the ultrasound transducer through the proximal end of the handle and through a corresponding interior conduit formed in and extending longitudinally along the longitudinal shaft of the handle.

The array of ultrasonic energy generation elements generally defines an axial length along the longitudinal shaft of the ultrasound probe of between about 8 millimeters and about 12 millimeters. In addition, the tactile feeler probe typically extends distally beyond the distal end of the longitudinal shaft of the ultrasound probe such that the longitudinal shaft and the feeler probe tip of the tactile feeler probe collectively define an axial length of the tactile feeler probe beyond the array of side-firing ultrasonic energy generation elements of between about 8 millimeters and about 12 millimeters.

The present disclosure also provides for a medical diagnostic instrument wherein the at least one hollow receiver member is mounted with respect to a distal portion of the longitudinal shaft of the ultrasound probe; and wherein the channel in or adjacent to the handle of the instrument defines at least a first longitudinal axis and the at least one hollow receiver member defines at least a second longitudinal axis, the first and second longitudinal axes being substantially aligned with one another. The present disclosure also provides for a medical diagnostic instrument wherein the at least one hollow receiver member includes a first hollow receiver member and a second hollow receiver member mounted with respect to the longitudinal shaft of the ultrasound probe, each hollow receiver member configured and dimensioned to receive the K-wire to permit the instrument to be slidably mounted thereto for purposes of guiding the ultrasound and tactile feeler probes axially relative to the desired anatomical location; and wherein the first hollow receiver member is mounted with respect to a distal portion of the longitudinal shaft of the ultrasound probe and the second hollow receiver member is mounted with respect to a proximal end of the ultrasound probe. The present disclosure also provides for a medical diagnostic instrument wherein at least a portion of the second hollow receiver member is mounted with respect to the handle.

The present disclosure also provides for a medical diagnostic instrument wherein the at least one hollow receiver member extends from a distal portion of the longitudinal shaft of the ultrasound probe to a proximal end of the ultrasound probe. The present disclosure also provides for a medical diagnostic instrument wherein at least a portion of the at least one hollow receiver member is mounted with respect to the handle.

The present disclosure also advantageously provides a medical diagnostic system for use in conjunction with bone tissue that includes:
a medical diagnostic instrument, the instrument including: a handle, the handle being disposable proximate an operator of the instrument, the handle being further configured and dimensioned to permit the operator to manually grasp the instrument and manipulate the instrument relative to the spine of a human patient; an ultrasound probe, the ultrasound probe including a longitudinal shaft extending distally from the handle and terminating in a distal end, and an ultrasound transducer mounted to the longitudinal shaft proximate the distal end thereof, the ultrasound transducer including an array of side-firing ultrasonic energy generation elements extending along the longitudinal shaft, wherein the ultrasound transducer and the distal end are cooperatively configured, oriented, and dimensioned to permit the operator to insert the ultrasound transducer and the distal end into a pedicle screw pilot hole formed in the spine of the human patient such that the array of side-firing ultrasonic energy generation elements of the ultrasound transducer extends axially along, and is positioned against, a selected portion of a side wall of the pedicle screw pilot hole, and to permit the operator to obtain thereat a corresponding two-dimensional image of the selected portion of the side wall for visual inspection by the operator for purposes of detecting ultrasonically-detectable cortical breaches located therein; a tactile feeler probe mounted with respect to the ultrasound probe, the tactile feeler probe including a longitudinal shaft mounted with respect to the longitudinal shaft of the ultrasound probe and extending distally therefrom beyond the distal end thereof, and a feeler probe tip defined at a distal end of the longitudinal shaft of the tactile feeler probe, the feeler probe tip and the longitudinal shaft of the tactile feeler probe being cooperatively configured and dimensioned to permit the operator to insert the feeler probe tip and the longitudinal shaft of the tactile feeler probe into the pedicle screw pilot hole such that the feeler probe tip is positioned against the selected portion of the side wall of the pedicle screw pilot hole, and to permit the operator to perform thereat a tactile inspection of the selected portion of the side wall of the pedicle screw pilot hole for purposes of detecting manually-detectable cortical breaches located therein; at least one hollow receiver member mounted with respect to the longitudinal shaft of the ultrasound probe, the at least one hollow receiver member configured and dimensioned to receive a K-wire to permit the instrument to be slidably mounted thereto for purposes of guiding the ultrasound and tactile feeler probes axially relative to the pedicle screw pilot hole; and a first cable assembly for carrying electrical signals to and from the ultrasound transducer in accordance with an ultrasonic imaging mode of use of the instrument, the cable assembly including a proximal end including a first electrical connector for connecting the instrument to a corresponding ultrasound console and current carrying wires extending distally from the electrical connector, through the longitudinal shaft of the ultrasound probe and to the ultrasound transducer; an ultrasound console including a processor for controlling the medical diagnostic instrument, a display for displaying two-dimensional ultrasonic images obtained therefrom by an operator thereof, and a port for receiving a corresponding cable connector; and a second cable assembly for carrying electrical signals to and from the ultrasound console, the second cable assembly including a second electrical connector coupled to a the port associated with the ultrasound console, a third electrical connector coupled to the first electrical connector, and current carrying wires extending therebetween.

The disclosed system may further include and/or be adapted to operate with an ultrasound console including a processor for controlling the medical diagnostic instrument, a display for displaying two-dimensional ultrasonic images obtained therefrom by an operator thereof, and a port for receiving a corresponding cable connector; and a second cable assembly for carrying electrical signals to and from the ultrasound console, the second cable assembly including a second electrical connector coupled to a the port associated with the ultrasound console, a third electrical connector coupled to the first electrical connector, and current carrying wires extending therebetween.

Still further, the present disclosure provides an advantageous method of exploring a desired anatomical location (e.g., a pedicle screw pilot hole formed in the spine of a human patient for cortical breaches located in the axially-extending side-walls thereof) that includes: presenting a medical diagnostic instrument, the instrument including: a handle; an ultrasound probe, the ultrasound probe including a longitudinal shaft extending distally from the handle and terminating in a distal end, and an ultrasound transducer mounted to the longitudinal shaft proximate the distal end thereof, the ultrasound transducer including an array of side-firing ultrasonic energy generation elements extending along the longitudinal shaft; a tactile feeler probe mounted with respect to the ultrasound probe, the tactile feeler probe including a longitudinal shaft mounted with respect to the longitudinal shaft of the ultrasound probe and extending distally therefrom beyond the distal end thereof, and a feeler probe tip defined at a distal end of the longitudinal shaft of the tactile feeler probe; and at least one hollow receiver member mounted with respect to the longitudinal shaft of the ultrasound probe, the at least one hollow receiver member configured and dimensioned to receive a K-wire to permit the instrument to be slidably mounted thereto for purposes of guiding the ultrasound and tactile feeler probes axially relative to the pedicle screw pilot hole;

mounting and sliding the medical diagnostic instrument along the K-wire to guide the ultrasound and tactile feeler probes axially relative to the pedicle screw pilot hole during a minimally invasive surgical procedure;

employing the handle to manually grasp and manipulate the medical diagnostic instrument relative to the spine of a human patient, including inserting the ultrasound transducer and the distal end of the longitudinal shaft of the ultrasound probe, and the feeler probe tip and the longitudinal shaft of the tactile feeler probe into a pedicle screw pilot hole formed in the spine of the human patient;

positioning the array of side-firing ultrasonic energy generation elements of the ultrasound transducer relative to a selected portion of a side wall of the pedicle screw pilot hole such that the array of side-firing ultrasonic energy generation elements extends axially along, and is positioned against, the selected portion of a side wall of the pedicle screw pilot hole;

employing the array of side-firing ultrasonic energy generation elements of the ultrasound transducer to obtain a two-dimensional image of the selected portion of the side wall for visual inspection for purposes of detecting ultrasonically-detectable cortical breaches located therein;

positioning the feeler probe tip of the tactile feeler probe relative to the selected portion of the side wall of the pedicle screw pilot hole such that the feeler probe tip is positioned against the side wall of the pedicle screw pilot hole;

employing the feeler probe tip of the tactile feeler probe to perform a tactile inspection of the selected portion of the side wall for purposes of detecting manually-detectable cortical breaches located therein; and performing the two positioning and the two employing steps without removing any of the ultrasound transducer or the distal end of the longitudinal shaft of the tactile feeler probe or the feeler probe tip of the longitudinal shaft of the tactile feeler probe from the pedicle screw pilot hole.

Additional features, functions and benefits of the present disclosure will be apparent from the detailed description which follows, particularly when read in conjunction with the accompanying figures.

BRIEF DESCRIPTION OF THE DRAWINGS

So that those having ordinary skill in the art to which the subject disclosure appertains will more readily understand how to construct and employ the systems, apparatus and methods of the subject disclosure, reference may be had to the drawings wherein:

FIGS. 2-7 are side elevational views of an exemplary medical diagnostic instrument in accordance with the present disclosure;

FIG. 7A is a partial side elevational view of an alternative exemplary medical diagnostic instrument in accordance with the present disclosure;

FIGS. 8 and 9 are side elevational and close-up side detail views, respectively, of a further embodiment of a medical diagnostic instrument in accordance with the present disclosure;

FIGS. 10 and 11 are respective side elevational and side detail views of a further exemplary embodiment of a medical diagnostic instrument in accordance with the present disclosure;

FIGS. 20-25 illustrate various known screw placement techniques used with respect to different spinal levels;

FIGS. 42-50 set forth information associated with tests conducted with respect to animal vertebral bodies using an ultrasound probe in accordance with embodiments of the present disclosure;

FIGS. 51-55 set forth information associated with tests conducted with respect to human cadaveric subjects in accordance with embodiments of the present disclosure;

FIG. 60 is a side perspective view of another exemplary embodiment of a medical diagnostic instrument in accordance with the present disclosure for use in conjunction with a K-wire during minimally invasive spine surgery;

DESCRIPTION OF EXEMPLARY EMBODIMENT(S)

In accordance with embodiments of the present disclosure, advantageous medical diagnostic instruments, systems and methods are provided for use during a broad variety of spinal surgical applications. The present disclosure provides improved equipment and advantageous methods for combining the comfort and familiarity of tactile inspection techniques with increasingly effective ultrasound imaging techniques to assist surgeons, for example, in quickly and conveniently inspecting pilot holes for bone tissue defects prior to pedicle screw implantation.

Figure 1:
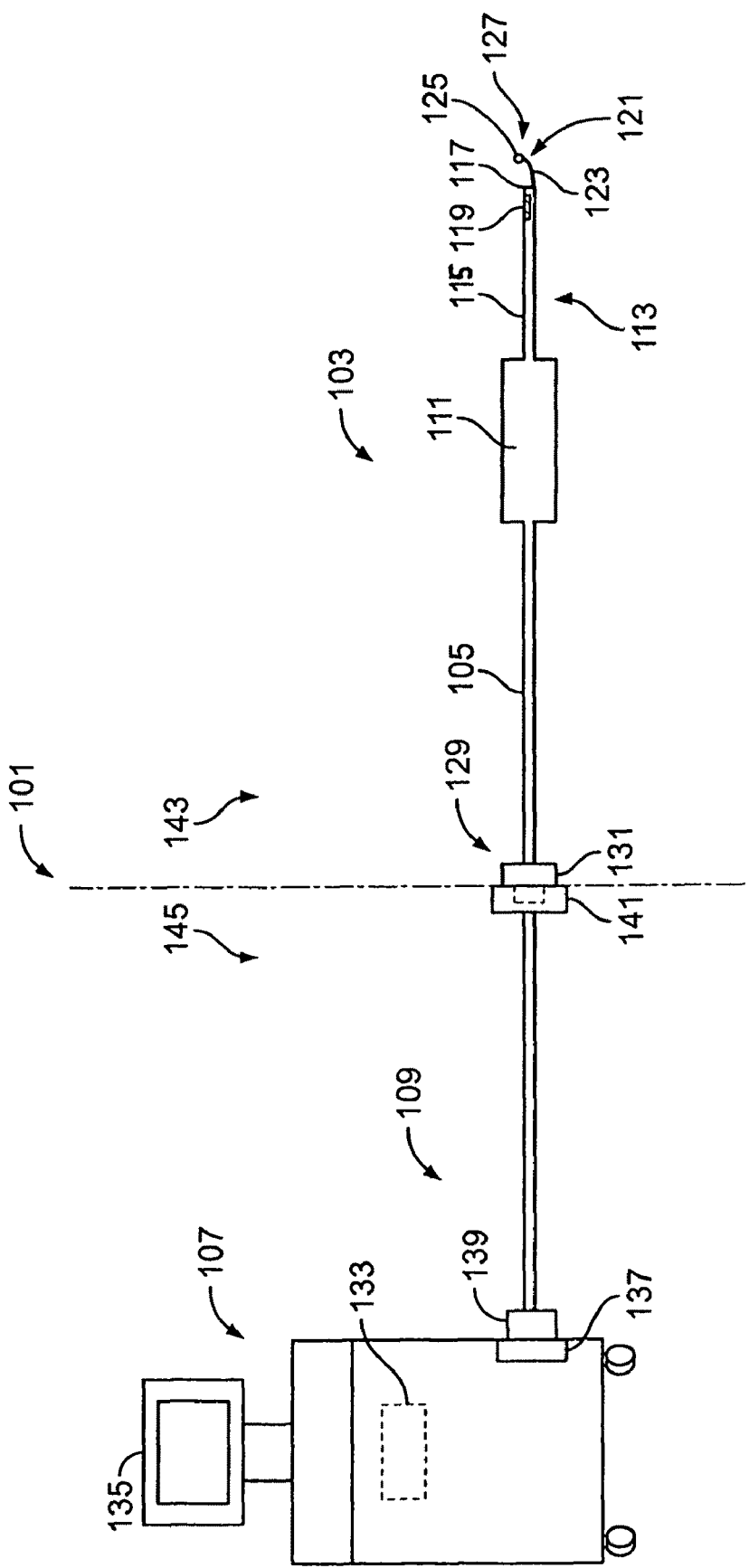
FIG. 1 is schematic side elevational view of a medical diagnostic system in accordance with the present disclosure, the system including a medical diagnostic instrument, an ultrasound console, and associated cable assemblies for establishing communication therebetween.

Referring now to FIG. 1, a medical diagnostic system 101 in accordance with embodiments of the present disclosure is shown. The system 101 includes a medical diagnostic instrument 103 which may include a first cable assembly 105. The system 103 also includes an ultrasound console 107 and a second cable assembly 109.

The instrument 103 includes a handle 111. The handle 111 is disposable proximate an operator (not shown) of the instrument 103 and is configured and dimensioned to permit the operator (not shown) to manually grasp the instrument 103, and to manipulate the instrument 103 relative to the spine of a human patient (not shown).

The instrument 103 further includes an ultrasound probe 113. The ultrasound probe 113 includes a longitudinal shaft 115 extending distally from the handle 111 and terminating in a distal end 117. The ultrasound probe 113 further includes an ultrasound transducer 119 mounted to the longitudinal shaft 115 proximate the distal end 117 thereof. The ultrasound transducer 119 includes an array of side-firing ultrasonic energy generation elements (not separately shown) extending along the longitudinal shaft 115.

The ultrasound transducer 119 and the distal end 117 are cooperatively configured, oriented, and dimensioned to permit the operator (not shown) to insert the ultrasound transducer 119 and the distal end 117 into a pedicle screw pilot hole (not shown) formed in the spine of the human patient (not shown) such that the array of side-firing ultrasonic energy generation elements of the ultrasound transducer 119 extends axially along, and is positioned against, a selected portion of a side wall (not shown) of the pedicle screw pilot hole, and to permit the operator to obtain thereat a corresponding two-dimensional image (not shown) of the selected portion of the side wall for visual inspection by the operator for purposes of detecting ultrasonically-detectable cortical breaches located therein (not shown).

The instrument 103 further includes a tactile feeler probe 121 mounted with respect to the ultrasound probe 113, the tactile feeler probe 121 including a longitudinal shaft 123 mounted with respect to the longitudinal shaft 115 of the ultrasound probe 113 and extending distally therefrom beyond the distal end 117 thereof, and a feeler probe tip 125 defined at a distal end 127 of the longitudinal shaft 123 of the tactile feeler probe 121, the feeler probe tip 125 and the longitudinal shaft 123 of the tactile feeler probe 121 being cooperatively configured and dimensioned to permit the operator (not shown) to insert the feeler probe tip 125 and the longitudinal shaft 123 of the tactile feeler probe 121 into the pedicle screw pilot hole (not shown) such that the feeler probe tip 125 is positioned against the selected portion of the side wall of the pedicle screw pilot hole (not shown), and to permit the operator to perform thereat a tactile inspection of the selected portion of the side wall of the pedicle screw pilot hole for purposes of detecting manually detectable cortical breaches located therein (not shown).

As indicated above, the instrument 103 may further include a first cable assembly 105. The first cable assembly 105 may be configured and arranged to carry electrical signals to and from the ultrasound transducer 119 in accordance with an ultrasonic imaging mode of use of the instrument 103. The first cable assembly 105 may include a proximal end 129 including a first electrical connector 131 for connecting the instrument 103 to a corresponding ultrasound console 107 and current carrying wires (not separately shown) extending distally from the electrical connector 131, through the longitudinal shaft 115 of the ultrasound probe 113 and to the ultrasound transducer 119.

The ultrasound console 107 includes a processor 133 for controlling the instrument 103, a display 135 for displaying two-dimensional ultrasonic images obtained from the instrument 103 by an operator thereof, and a port 137 for receiving a corresponding cable connector.

As indicated above, the system 101 includes a second cable assembly 109 for carrying electrical signals to and from the ultrasound console 107. The second cable assembly 109 includes a second electrical connector 139 coupled to a the port 137 associated with the ultrasound console 107, a third electrical connector 141 coupled to the first electrical connector 131, and current carrying wires (not separately shown) extending therebetween.

The connection between the third electrical connector 141 of the second cable assembly 109 and the first electrical connector 131 of the first cable assembly may be an umbilical connection between a disposable portion 143 of the medical diagnostic system 101 including the medical diagnostic instrument 103, and a non-disposable portion 145 of the medical diagnostic system 101 including the ultrasound console 107 and the second cable assembly 109.

Figure 2:
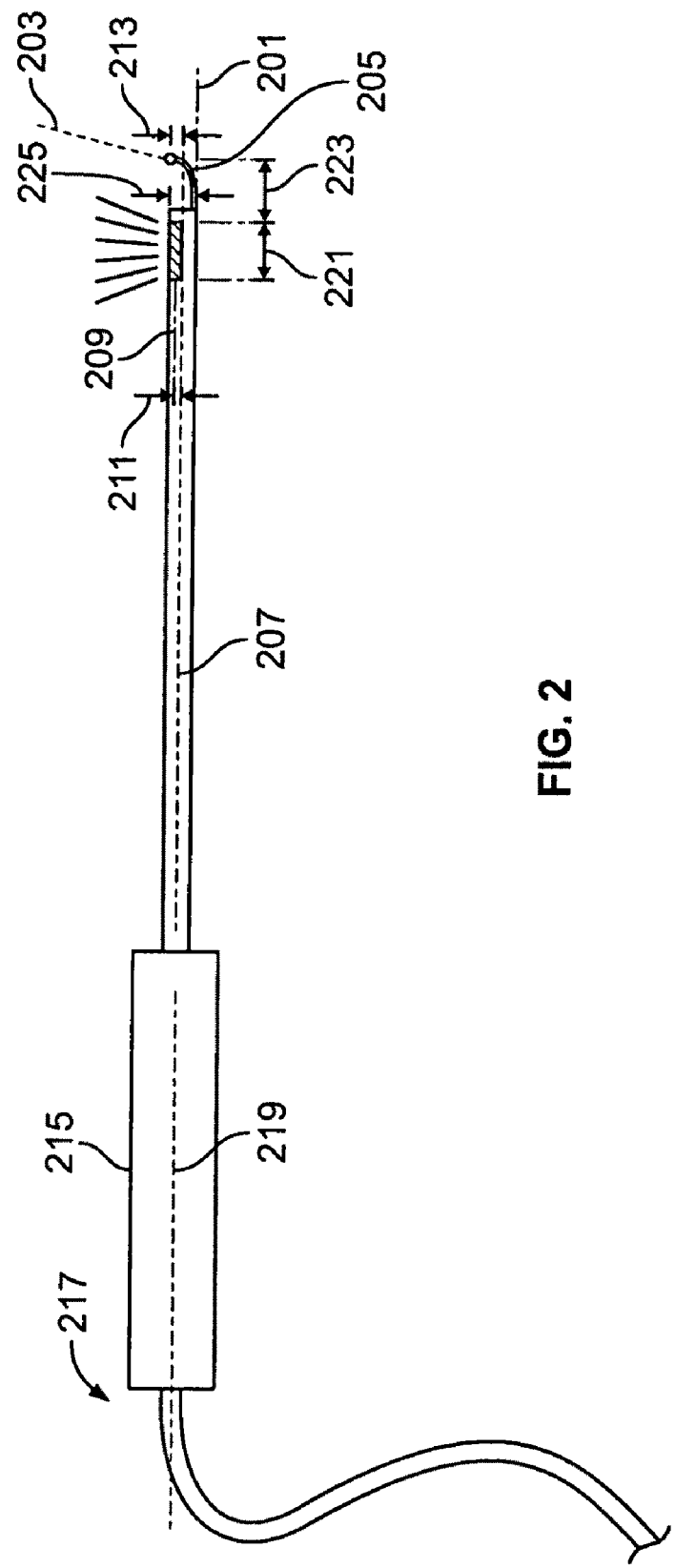

Turning now to FIGS. 1 and 2, the longitudinal shaft 123 of the tactile feeler probe 121 may define a longitudinal axis 201 along which the longitudinal shaft 123 of the tactile feeler probe 121 extends distally from the longitudinal shaft 115 of the ultrasound probe 113, and a longitudinal axis 203 along which the longitudinal shaft 123 of the tactile feeler probe 121 extends distally to the feeler probe tip 125, and a bend 205 formed therebetween such that the longitudinal axis 201 and the longitudinal axis 203 collectively define a first plane (represented in FIG. 2 by the plane in which FIG. 2 appears). The longitudinal shaft 115 of the ultrasound probe 113 may define a longitudinal axis 207 along which the longitudinal shaft 115 of the ultrasound probe 113 extends distally from the handle 111. The side-firing ultrasonic energy generation elements of the array thereof (not separately shown) may define a longitudinal axis 209 along which the array of side-firing ultrasonic energy generation elements extends.

As indicated in FIG. 2 at reference numeral 211, the longitudinal axis 209 associated with the side-firing ultrasonic energy elements of the array thereof may be radially offset from the longitudinal axis 207 associated with the longitudinal shaft 115 of the ultrasound probe 113. In such circumstances, the longitudinal axis 207 and the longitudinal axis 209 may collectively define a second plane (represented in FIG. 2 by the plane in which FIG. 2 appears) that is coplanar with the first plane.

As indicated in FIG. 2 at reference numeral 213, the feeler probe tip 125 may be radially offset from the longitudinal axis 207 associated with the longitudinal shaft 115 of the ultrasound probe 113. In such circumstances, each of the feeler probe tip 125 and the longitudinal axis 209 associated with the array of side-firing ultrasonic energy generation elements may be offset from the longitudinal axis 207 in a common radial direction therefrom such that the feeler probe tip 125 and the array of side-firing ultrasonic energy generation elements are rotationally aligned with each other relative to the longitudinal shaft 115 of the ultrasound probe 113. Alternatively (not shown in FIG. 2), the feeler probe tip 125 may be disposed on the longitudinal axis 207 associated with the longitudinal shaft 115 of the ultrasound probe 113.

Still referring to FIG. 2, the handle 111 may include a longitudinal shaft 215 extending proximally from the ultrasound probe 113 and terminate in a proximal end 217. The longitudinal shaft 215 may define a longitudinal axis 219 along which the handle 111 extends proximally from the ultrasound probe 113. As shown in FIG. 2, the longitudinal axis 217 may be disposed in the first plane (represented in FIG. 2 by the plane in which FIG. 2 appears). In such circumstances, the longitudinal axis 219 associated with the handle may be positioned and oriented coaxially with respect to the longitudinal axis 207 associated with the longitudinal shaft 115 of the ultrasound probe 113 such that the handle 211 and the ultrasound probe 113 are longitudinally aligned with each other.

As indicated in FIG. 2 at reference numeral 221, the array of side-firing ultrasonic energy generation elements may define an axial length along the longitudinal shaft 115 of the ultrasound probe 113 of between about 8 millimeters and about 12 millimeters. For example, the array of side-firing ultrasonic energy generation elements may define an axial length along the longitudinal shaft 115 of the ultrasound probe 113 of about 10 millimeters.

As indicated in FIG. 2 at reference numeral 223, the tactile feeler probe 121 extending distally beyond the distal end 117 of the longitudinal shaft 115 of the ultrasound probe 113 may include wherein the longitudinal shaft 123 and the feeler probe tip 125 of the tactile feeler'probe 121 may collectively define an axial length of the tactile feeler probe 121 beyond the array of side-firing ultrasonic energy generation elements of between about 8 millimeters and about 12 millimeters. For example, the feeler probe tip 125 of the tactile feeler probe 121 may collectively define an axial length of the tactile feeler probe 121 beyond the array of side-firing ultrasonic energy generation elements of about 10 millimeters.

As indicated in FIG. 2 at reference numeral 225, the ultrasound transducer 119 and the distal end 117 being cooperatively configured, oriented, and dimensioned to permit the operator to insert the ultrasound transducer 119 and the distal end 117 into a pedicle screw pilot hole formed in the spine of the human patient (not shown) includes wherein the ultrasound transducer 119 and the distal end 117 define a transverse width or diameter of between about 2 millimeters and 4 millimeters. For example, the ultrasound transducer 119 and the distal end 117 define a transverse width or diameter of about 3 millimeters.

As shown in FIGS. 1 and 2, the feeler probe tip 125 may be a ball tip. The array of side-firing ultrasonic energy generation elements associated with the ultrasound transducer 119 may be a linear array. Alternatively, the array of side-firing ultrasonic energy generation elements associated with the ultrasound transducer 119 may be a phased array. Other types of arrays are possible as well.

Turning now to FIG. 3, a medical diagnostic instrument 301 in accordance with embodiments of the present disclosure is shown. The instrument 301 may be structurally and functionally similar to the instrument 103 discussed above with reference to FIGS. 1 and 2, with some differences. The instrument 301 includes a tactile feeler probe 303 that is mounted with respect to the ultrasound probe 305 such that the longitudinal shaft 307 of the tactile feeler probe 303 is supported, cantilever-style, by the longitudinal shaft 309 of the ultrasound probe 305. Also as shown, at least some longitudinal overlap exists between the longitudinal shaft 307 of the tactile feeler probe 303 and the longitudinal shaft 309 of the ultrasound probe. In the embodiment shown in FIG. 3, the longitudinal shaft 307 of the tactile feeler probe 303 includes no major bends and is mounted atop the longitudinal shaft 309 of the ultrasound probe 305.

Turning now to FIG. 4, a medical diagnostic instrument 401 in accordance with embodiments of the present disclosure is shown. The instrument 401 may be structurally and functionally similar to the instrument 103 discussed above with reference to FIGS. 1 and 2, with some differences. The instrument 401 includes a tactile feeler probe 403 that is mounted with respect to the ultrasound probe 405 such that the longitudinal shaft 407 of the tactile feeler probe 403 is supported, cantilever-style, by the longitudinal shaft 409 of the ultrasound probe 405. Also as shown, at least some longitudinal overlap exists between the longitudinal shaft 407 of the tactile feeler probe 403 and the longitudinal shaft 409 of the ultrasound probe. In the embodiment shown in FIG. 4, the longitudinal shaft 407 of the tactile feeler probe 403 includes no major bends. A proximal end 411 of the longitudinal shaft 407 of the tactile feeler probe 403 is lodged within a complementary cavity 413 formed in the longitudinal shaft 409 of the ultrasound probe 405 adjacent the distal end 415 thereof.

Referring now to FIG. 5, a medical diagnostic instrument 501 in accordance with embodiments of the present disclosure is shown. The instrument 501 may be structurally and functionally similar to the instrument 103 discussed above with reference to FIGS. 1 and 2, with some differences. The instrument 501 includes no tactile feeler probe. Otherwise, the instrument 501 is configured and dimensioned substantially identically to the instrument 103.

A medical diagnostic instrument 601 in accordance with embodiments of the present disclosure is shown in FIG. 6. The instrument 601 is configured and dimensioned substantially identically to the instrument 103, with differences as discussed below in the handle 603 of the instrument 601 as compared to the handle 111 of the instrument 103. The longitudinal shaft 605 of the handle 603 defines a further longitudinal axis 607 disposed in the plane of FIG. 6 and along which the longitudinal shaft 605 of the handle 603 extends proximally to the proximal end 609 of the handle 603, and a bend 611 formed between the longitudinal axis 607 and the longitudinal axis 613 such that an angle defined between the longitudinal axis 607 and the longitudinal axis 615 is larger than an angle defined between the longitudinal axis 613 and the longitudinal axis 615, and such that the handle 603 functions as a bayonet handle relative to the ultrasound and feeler probes 617, 619.

Figures 7, 7A:
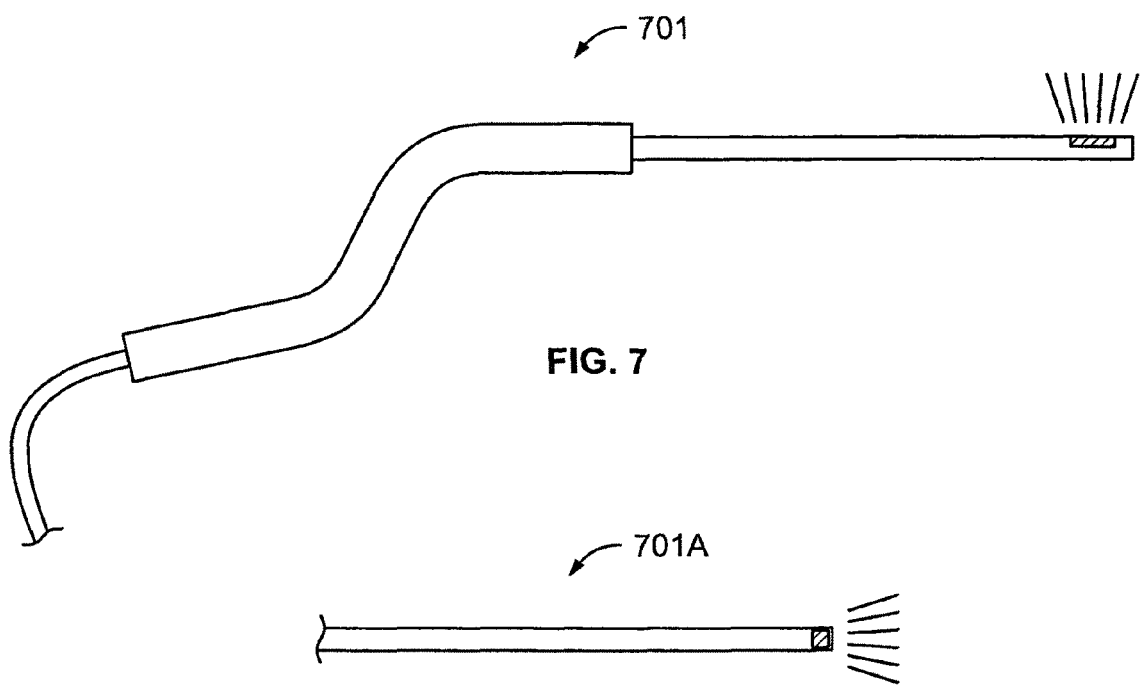

Turning now to FIG. 7, a medical diagnostic instrument 701 in accordance with embodiments of the present disclosure is shown. The instrument 701 may be structurally and functionally similar to the instrument 601 discussed above with reference to FIG. 6, with some differences. The instrument 701 includes no tactile feeler probe. Otherwise, the instrument 701 is configured and dimensioned substantially identically to the instrument 601. Of note, the ultrasonic energy generation elements may be oriented on opposite sides of the ultrasound probe, as will be apparent to persons skilled in the art. In addition, FIG. 7A shows the distal end of an alternative version of the disclosed diagnostic medical instrument 701A in which the array of ultrasonic energy generation elements are axially aligned with the ultrasound probe such that the ultrasound energy from the ultrasound probe is directed substantially axially, i.e., in a substantially forward direction.

FIGS. 8 and 9 include respective side and close-up cutaway side views of a medical diagnostic instrument 801 in accordance with embodiments of the present disclosure. The instrument 801 may be structurally and functionally similar to the instrument 103 discussed above with reference to FIGS. 1 and 2, with some differences. The handle 803 of the diagnostic instrument 801 includes a housing 805. The ultrasound probe 807 is mounted with respect to the handle 803 such that the longitudinal shaft 809 of the ultrasound probe 807 is supported, cantilever-style, by the handle housing 805. The tactile feeler probe 811 is mounted with respect to the ultrasound probe 807 such that the longitudinal shaft 813 of the tactile feeler probe 811 is supported, cantilever-style, by the longitudinal shaft 809 of the ultrasound probe 807. In accordance with some embodiments of the present disclosure, including the embodiment shown in FIGS. 8 and 9, there is no overlap between the longitudinal shaft 809 of the ultrasound probe and the longitudinal shaft 813 of the tactile feeler probe 811. Instead, the tactile feeler probe 811 is mounted directly to the distal end 815 of the longitudinal shaft 809 of the ultrasound probe 807 via a proximal shoulder portion 817 of the tactile feeler probe 813.

Turning now to FIGS. 10 and 11, a medical diagnostic instrument 1001 in accordance with embodiments of the present disclosure is shown. The instrument 1001 may be structurally and functionally similar to the instrument 401 discussed above with reference to FIG. 4, with some differences. In accordance with some embodiments of the present disclosure, including the embodiment shown in FIGS. 10 and 11, there is no overlap between the longitudinal shaft 1003 of the ultrasound probe 1005 and the longitudinal shaft 1007 of the tactile feeler probe 1009. Instead, the tactile feeler probe 1009 is mounted directly to the distal end 1011 of the longitudinal shaft 1003 of the ultrasound probe 1005 via a proximal shoulder portion 1013 of the tactile feeler probe 100.

Figure 12:
FIGS. 12, 13 and 14 are top plan, side elevational, and bottom plan views, respectively, of an additional exemplary embodiment of a medical diagnostic instrument in accordance with the present disclosure.
Figure 13:
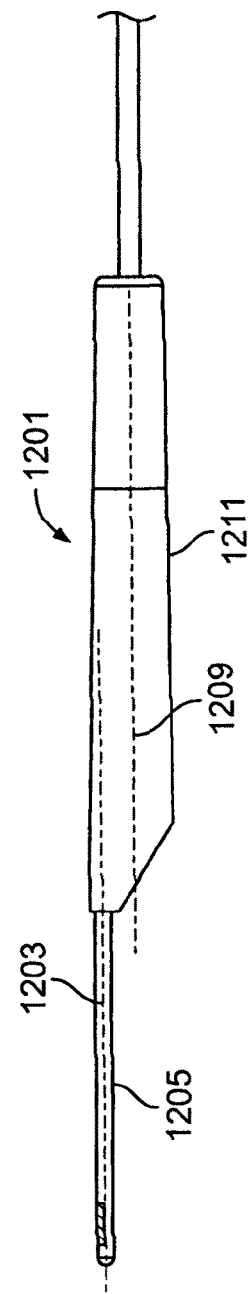
Figure 14:
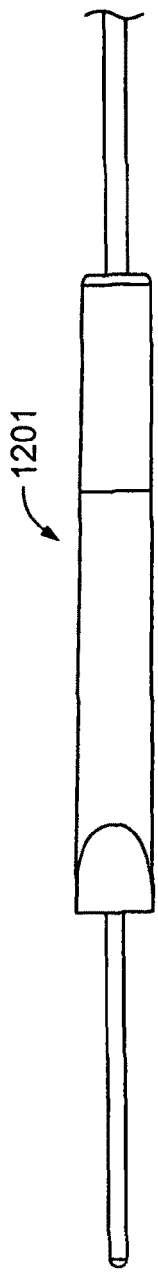

Referring now to FIGS. 12, 13 and 14, a medical diagnostic instrument 1201 in accordance with embodiments of the present disclosure is shown. The instrument 1201 may be structurally and functionally similar to the instrument 501 discussed above with reference to FIG. 5, with some differences. The longitudinal axis 1203 associated with the longitudinal shaft 1205 of the ultrasound probe 1207 may be radially offset from the longitudinal axis 1209 associated with the longitudinal shaft 1211 of the handle.

Figure 15:
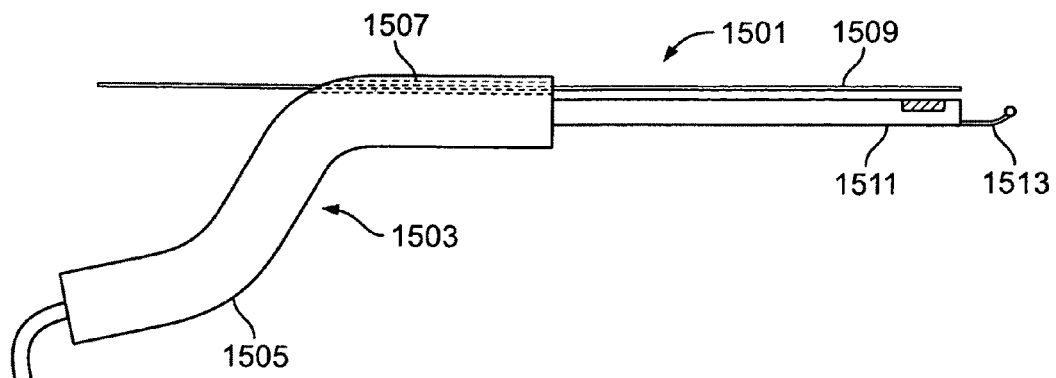
FIG. 15 is a side elevational view of an exemplary embodiment of a medical diagnostic instrument in accordance with the present disclosure for use in conjunction with a K-wire during minimally invasive spine surgery.

Turning now to FIG. 15, a medical diagnostic instrument 1501 in accordance with embodiments of the present disclosure is shown. The instrument 1501 may be structurally and functionally similar to the instrument 601 discussed above with reference to FIG. 6, with certain additional features. The handle 1503 of the diagnostic instrument 1501 includes a housing 1505. In the housing 1505 of the handle 1503 is formed a channel 1507 configured and dimensioned to receive a K-wire 1509 to permit the instrument 1501 to be slidably mounted thereto for purposes of guiding the ultrasound and tactile feeler probes 1511, 1513 axially relative to the pedicle screw pilot hole, including during a minimally invasive surgical procedure, the channel 1507 being formed in the housing 1505 of the handle 1503 and extending through the handle 1503.

Figure 15A:
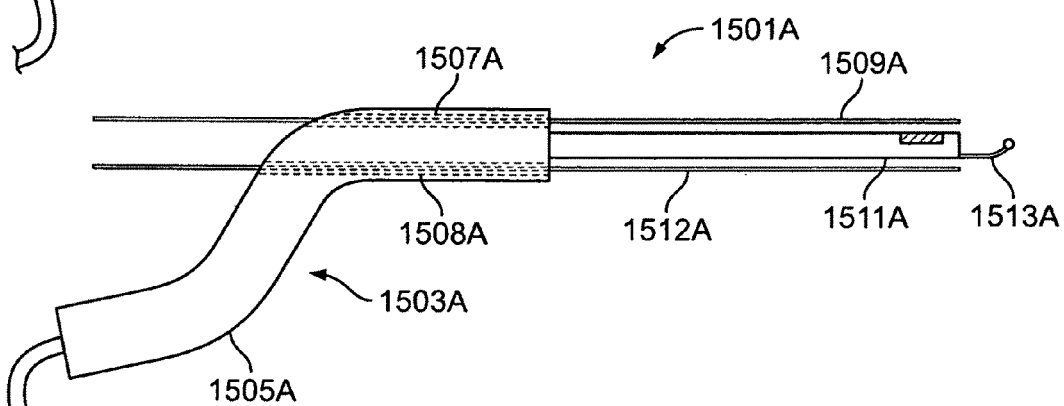
FIG. 15A is a side elevational view of an exemplary embodiment of a medical diagnostic instrument similar to the instrument of FIG. 15 in accordance with the present disclosure for use in conjunction with a K-wire (that may be introduced through alternative channels) during minimally invasive spine surgery.

With reference to FIG. 15A, an alternative medical diagnostic instrument 1501A is shown in which handle 1503A includes a housing 1505A that defines first channel 1507A and second channel 1508A. Both channels 1507A and 1508A are configured and dimensioned to receive a K-wire, e.g., K-wire 1509A and/or K-wire 1512A, to permit the instrument 1501A to be slidably mounted thereto for purposes of guiding the ultrasound and tactile feeler probes 1511A, 1513A axially relative to the pedicle screw pilot hole, including during a minimally invasive surgical procedure. Thus, the channels 1507A and 1508A are formed in the housing 1505A of the handle 1503A and extend therethrough. In use, the operator/surgeon would be free to select the channel to be used for K-wire introduction, e.g., based on whether the operator/surgeon desires to see the K-wire pass the ultrasound probe.

Figure 16:
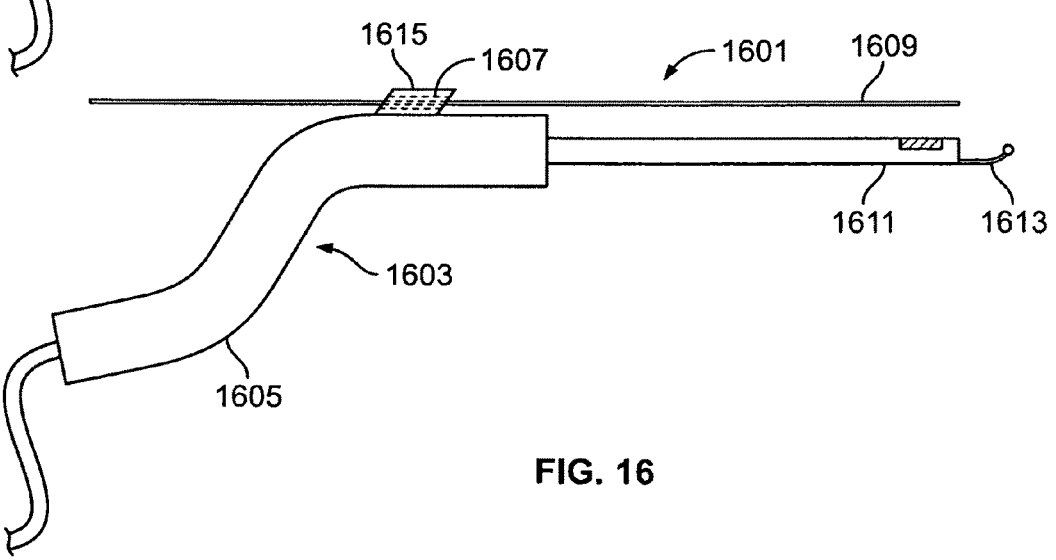
FIG. 16 is a side elevational view of another exemplary embodiment of a medical diagnostic instrument in accordance with the present disclosure for use in conjunction with a K-wire during minimally invasive spine surgery.

Turning now to FIG. 16, a medical diagnostic instrument 1601 in accordance with embodiments of the present disclosure is shown. The instrument 1601 may be structurally and functionally similar to the instrument 601 discussed above with reference to FIG. 6, with certain additional features. The handle 1603 of the diagnostic instrument 1601 includes a housing 1605. A channel 1607 is configured and dimensioned to receive a K-wire 1609 to permit the instrument 1601 to be slidably mounted thereto for purposes of guiding the ultrasound and tactile feeler probes 1611, 1613 axially relative to the pedicle screw pilot hole, including during a minimally invasive surgical procedure, the channel 1607 being formed in an extension 1615 of the housing 1605 of the handle 1603 and extending past the handle 1603.

With reference to FIG. 60, a medical diagnostic instrument 8001 in accordance with embodiments of the present disclosure is shown. Instrument 8001 may be structurally and functionally similar to the instrument 1501 discussed above with reference to FIG. 15, with some differences. In general, instrument 8001 includes at least one hollow receiver member 8017 mounted with respect to longitudinal shaft 8015 of ultrasound probe 8011. In general, the at least one hollow receiver member 8017 is configured and dimensioned to receive a K-wire or guidewire or the like (e.g., a wire similar to K-wire 1509 of FIG. 15) to permit the instrument 8001 to be slidably mounted thereto for purposes of guiding the ultrasound and tactile feeler probes 8011 and 8013 axially relative to the pedicle screw pilot hole, including during a minimally invasive surgical procedure.

The tactile feeler probe 8013 may or may not include a longitudinal shaft mounted with respect to the longitudinal shaft 8015 of the ultrasound probe 8011 and extending distally therefrom beyond the distal end thereof, and a feeler probe tip defined at a distal end of the longitudinal shaft of the tactile feeler probe 8013 (similar to instrument 103 of FIG. 1). The ultrasound probe 8011 typically includes an ultrasound transducer mounted to the longitudinal shaft 8015 proximate the distal end thereof, with the ultrasound transducer typically having an array of side-firing ultrasonic energy generation elements extending along the longitudinal shaft 8015 (similar to instrument 103 of FIG. 1 and instrument 1501 of FIG. 15). In exemplary embodiments, the tactile feeler probe 8013 may be mounted with respect to the ultrasound probe 8011 such that the longitudinal shaft of the tactile feeler probe 8013 is supported, cantilever-style, by the longitudinal shaft 8015 of the ultrasound probe 8011 (e.g., see instrument 301 of FIG. 3 or instrument 401 of FIG. 4). In other embodiments, there may be no overlap between the longitudinal shaft 8015 of the ultrasound probe 8011 and the longitudinal shaft of the tactile feeler probe 8013 (e.g., see instrument 801 of FIG. 8 or instrument 1001 of FIG. 10).

In one embodiment, the at least one hollow receiver member 8017 is positioned or mounted with respect to a distal portion of the longitudinal shaft 8015 of ultrasound probe 8011, although the present disclosure is not limited thereto. Rather, the at least one hollow receiver member 8017 may be positioned or mounted to any portion of the longitudinal shaft 8015 of ultrasound probe 8011.

In one embodiment and as shown in FIG. 60, handle 8003 of diagnostic instrument includes a housing 8005, the housing 8005 including a channel 8007 formed therein, with the channel 8007 also configured and dimensioned to receive the K-wire or guidewire or the like that is received in hollow receiver member 8017 to permit the instrument 8001 to be slidably mounted thereto for purposes of guiding the ultrasound and tactile feeler probes 8011 and 8013 axially relative to the pedicle screw pilot hole. In exemplary embodiments, channel 8007 extends through handle 8003. Alternatively, channel 8007 may be formed in an extension of the housing 8005 of the handle 8003 (e.g., similar to extension 1615 of FIG. 16). In one embodiment, the longitudinal axis defined by channel 8007 is substantially the same as and/or is substantially aligned with the longitudinal axis defined by the at least one hollow receiver member 8017 (i.e., the same K-wire 1509 would extend through channel 8007 and receiver member 8017). Alternatively, housing 8005 does not include channel 8007, and the K-wire or the like only travels through the at least one receiver member 8017 to permit the instrument 8001 to be slidably mounted thereto for guiding purposes.

Figure 60B:
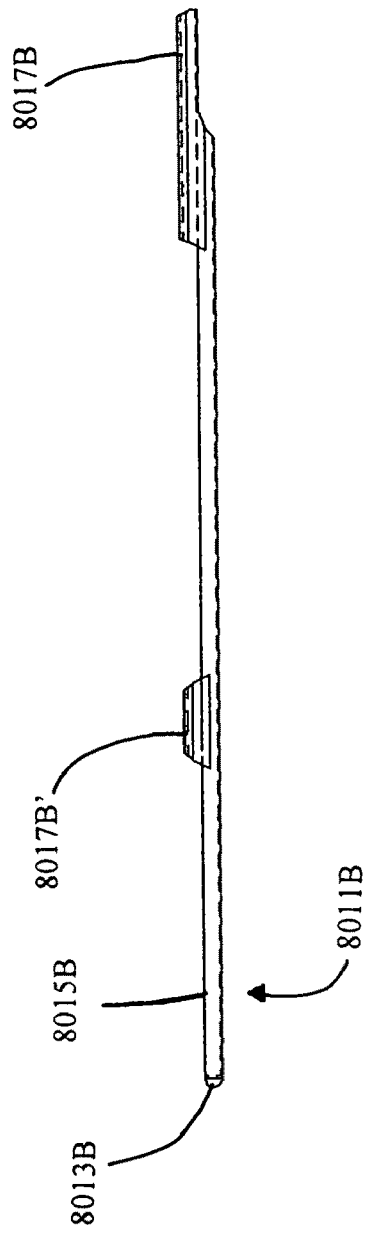
FIGS. 60A and 60B are side elevational views of alternative ultrasound probes having at least one hollow receiver member mounted thereto for use with a medical diagnostic instrument similar to the instrument of FIG. 60.
Figure 60A:
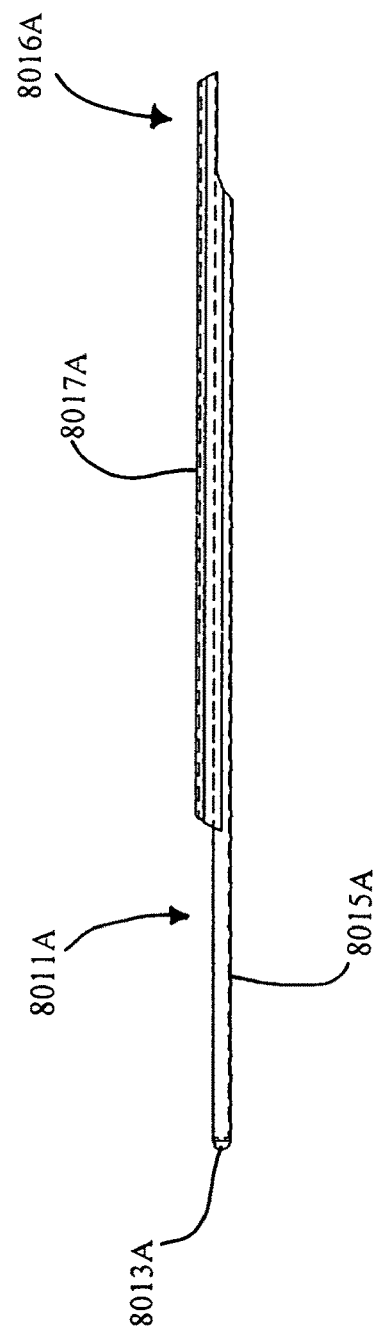

In another embodiment and as depicted in FIG. 60A, an ultrasound probe 8011A with tactile feeler probe 8013A for use with a medical diagnostic instrument similar to instrument 8001 is depicted. At least one hollow receiver member 8017A is mounted with respect to longitudinal shaft 8015A of ultrasound probe 8011A and extends from a portion (e.g., a distal portion) of the shaft 8015A to a proximal end 8016A of shaft 8015A. In general, hollow receiver member 8017A is configured and dimensioned to receive a K-wire or guidewire or the like to permit the medical diagnostic instrument to be slidably mounted thereto for guiding purposes.

In exemplary embodiments, the housing of the handle of the medical diagnostic instrument for use with probe 8011A may be configured and dimensioned to house and/or mount with respect to at least a portion of the proximal end 8016A of shaft 8015A. For example, at least a portion of the proximal end 8016A of shaft 8015A defines at least a portion of a channel through the housing of the handle of the medical diagnostic instrument for use with probe 8011A. The housing of the handle of the medical diagnostic instrument for use with probe 8011A may or may not include a separate channel through the handle for use with the K-wire (e.g., separate from proximal end 8016A housed in the housing).

In another embodiment and as shown in FIG. 60B, an ultrasound probe 8011B with tactile feeler probe 8013B for use with a medical diagnostic instrument similar to instrument 8001 is depicted. Probe 8011B includes a first hollow receiver member 8017B and a second hollow receiver member 8017B', with the first and second hollow receiver members 8017B, 8017B' being mounted with respect to longitudinal shaft 8015B of ultrasound probe 8011B. In general, first and second hollow receiver members 8017B, 8017B' are configured and dimensioned to receive a K-wire or guidewire or the like (e.g., wire 1509 of FIG. 15) to permit the medical diagnostic instrument to be slidably mounted thereto for guiding purposes.

In one embodiment, first hollow receiver member 8017B is positioned or mounted with respect to a proximal end of probe 8011B, and second hollow receiver member 8017B' is positioned or mounted with respect to a distal portion of probe 8011B, although the present disclosure is not limited thereto. The housing of the handle of the medical diagnostic instrument for use with probe 8011B may be configured and dimensioned to house and/or mount with respect to at least a portion of first hollow receiver member 8017B. For example, at least a portion of first hollow receiver member 8017B defines at least a portion of a channel through the housing of the handle of the medical diagnostic instrument for use with probe 8011B. The housing of the handle of the medical diagnostic instrument for use with probe 8011B may or may not include a separate channel through the handle for use with the K-wire (i.e., separate from first hollow receiver member 8017B housed in the housing). In exemplary embodiments, the longitudinal axis defined by the first hollow receiver member 8017B is substantially the same as and/or is substantially aligned with the longitudinal axis defined by the second hollow receiver member 8017B' (i.e., the same K-wire 1509 would extend through first hollow receiver member 8017B and second hollow receiver member 8017B').

Variations and modifications of the above-described medical diagnostic instruments are possible in accordance with embodiments of the present disclosure. In accordance with some such variations and modifications (not shown), the handle and the longitudinal shaft of the ultrasound probe (and/or the longitudinal shaft of the ultrasound probe and the hollow receiver members) are of unitary construction with respect to each other. Each of the above-described diagnostic instruments may be equipped with a cable assembly for carrying electrical signals to and from the ultrasound transducer in accordance with an ultrasonic imaging mode of use of the instrument, the cable assembly including a proximal end including an electrical connector for connecting the instrument to a corresponding ultrasound console and current carrying wires extending distally from the electrical connector to the ultrasound transducer at least partially via a corresponding interior conduit formed in and extending longitudinally along the longitudinal shaft of the ultrasound probe. Other variations and modifications are possible.

Thus, the present disclosure provides, inter alia, advantageously integrated medical diagnostic instruments, systems incorporating such instruments, and methods of use of such instruments and systems for the benefit of such surgical practitioners and their patients. Practitioners may employ the presently disclosed technology in connection with a broad variety of surgical applications, including with respect to any bone in the human body in which a screw may be inserted. For example and/or in particular, surgical practitioners may advantageously apply the presently disclosed technology for the benefit of spine patients, including with respect to the specific application of intrapedicular screw implantation.

Further details of the use of the presently disclosed technology with respect to the specific application of intrapedicular screw implantation are provided hereinbelow. Based at least in part on the results of testing performed in connection with the presently disclosed technology, the disclosed instruments, systems, and methods of the present disclosure can be seen to address a variety of compelling needs long felt by surgical practitioners. For example, the presently disclosed technology addresses the perpetually growing demand on the part of such professionals for effective instruments, systems and related surgical methods for use in connection with such applications as cervical spine surgery, thoracic spine surgery, lumbar spine surgery, and sacral spine surgery, including surgery performed for the benefit of patients suffering from spinal trauma, spinal tumors, degenerative spine disorders, scoliosis and other diseases and conditions.

Figure 18:
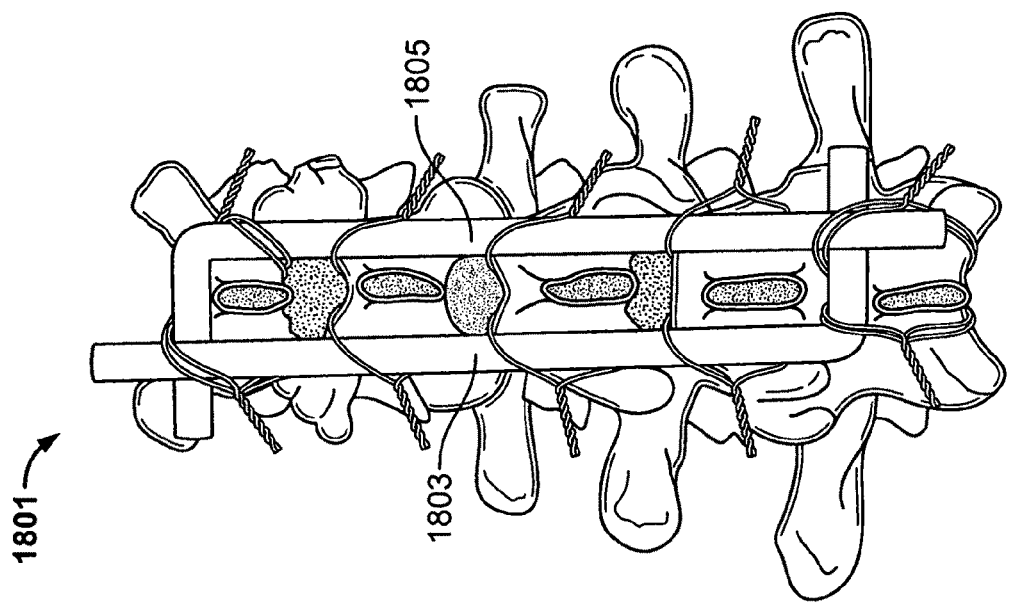
FIGS. 17, 18 and 19 illustrate various known spinal implant applications.
Figure 17:
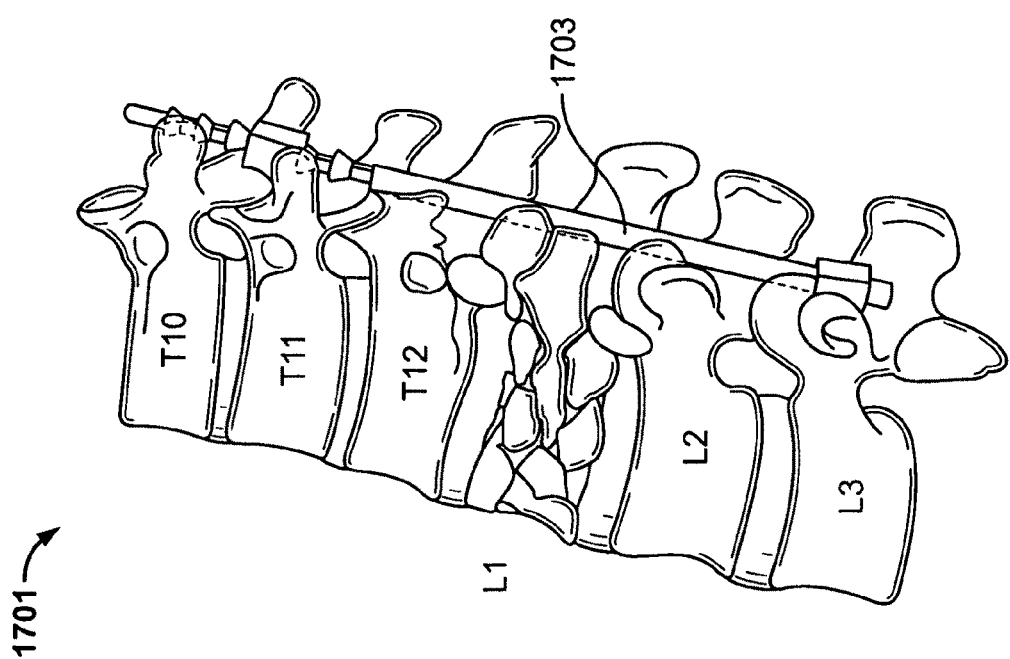
Figure 19:
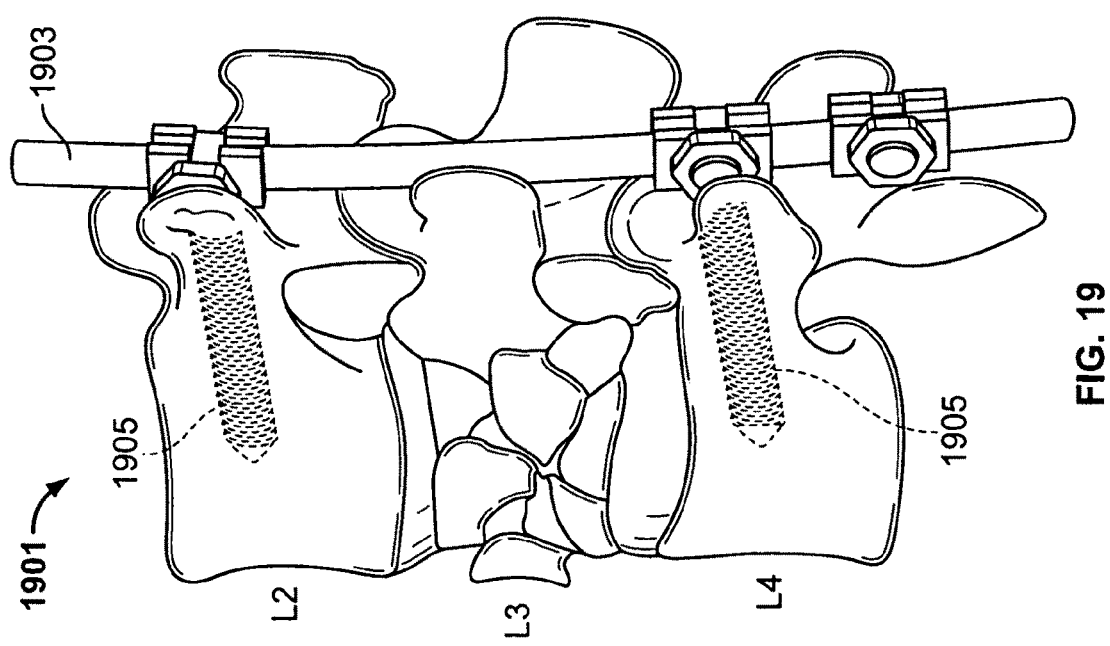

Turning now to FIGS. 17, 18, and 19, various known spinal implant applications are illustrated. A spinal implant 1701 shown in side elevational view in FIG. 17, including at least one spinal support rod 1703, is placed adjacent to and extending across multiple spinal levels including L3, L2, L1, T12, T11 and T10 to compensate for deterioration in or damage done to the L1 pedicle. Another spinal implant 1801 is shown in rear elevational view in FIG. 18, including angled and cross-connected spinal support rods 1803, 1805, each extending across a corresponding side of multiple spinal levels. A further spinal implant 1901 is shown in side elevational view in FIG. 19, including a spinal support rod 1903 placed adjacent to and extending across spinal levels L4, L3 and L2 to compensate for deterioration in or damage done to the L3 pedicle, such spinal implant 1901 including respective pedicle screws 1905 affixed to the adjacent L2 and L4 pedicles. The presently disclosed technology may be employed in conjunction with any or all such spinal implant applications, as well as spinal implant applications similar thereto.

Referring now to FIGS. 20, 21, 22, 23, 24 and 25, various known screw placement techniques are shown for use with respect to different spinal levels, including with respect to a first pedicle 2001 shown in rear elevational, top plan and side elevational views in FIGS. 20, 21, and 22, respectively, a second pedicle 2301 shown in rear elevational and top plan views in FIGS. 23 and 24, respectively, and a third pedicle 2501 shown in top plan view in FIG. 25. The presently disclosed technology may be employed in conjunction with any or all such pedicle screw placement techniques, as well as pedicle screw placement techniques similar thereto.

Figure 26:
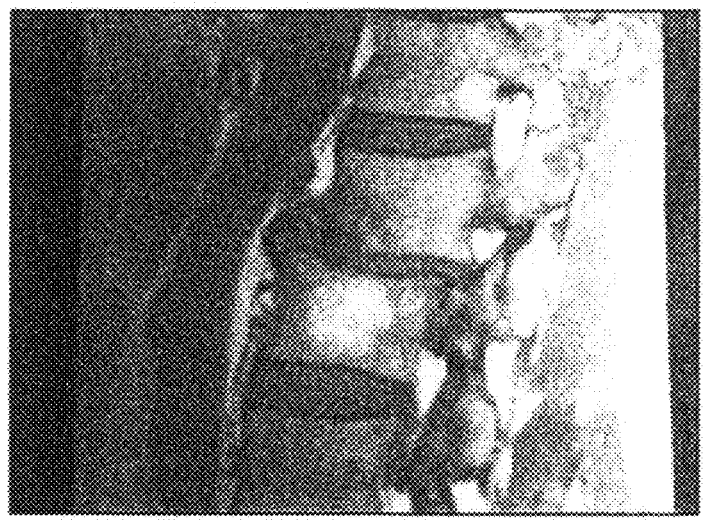
FIGS. 26-28 (L2/3 Listhesis), FIGS. 29-31 (L2 Burst Fracture), FIGS. 32-34 (L1 Burst Fracture), FIGS. 35-37 (Metastatic Bone Disease) and FIGS. 38-39 (Minimally Invasive Surgery) illustrate various examples of instrumented spine surgery in which the disclosed systems, apparatus and methods may be used for the benefit of spinal patients suffering from a variety of spinal diseases, degenerative conditions and/or diseases.
Figure 27:
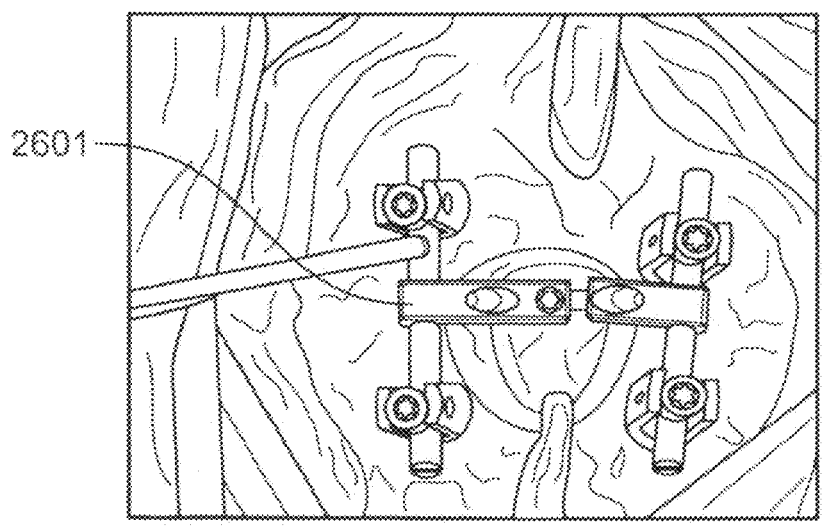
Figure 28:
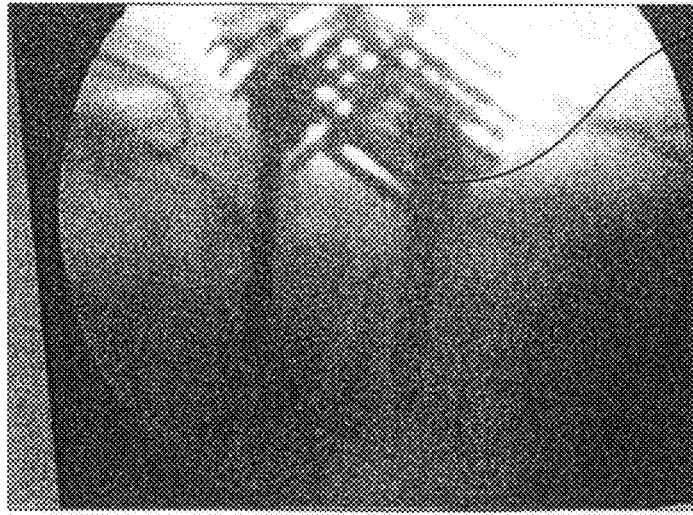
Figure 33:
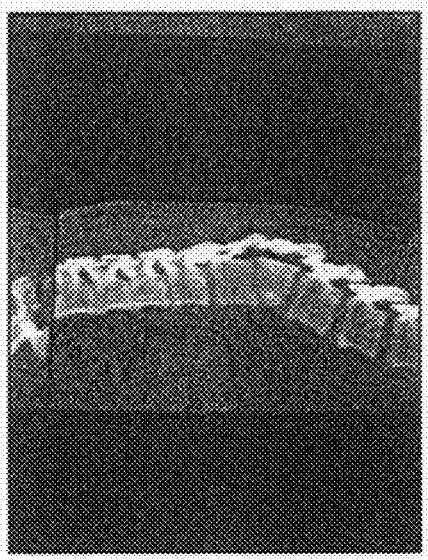
Figure 34:
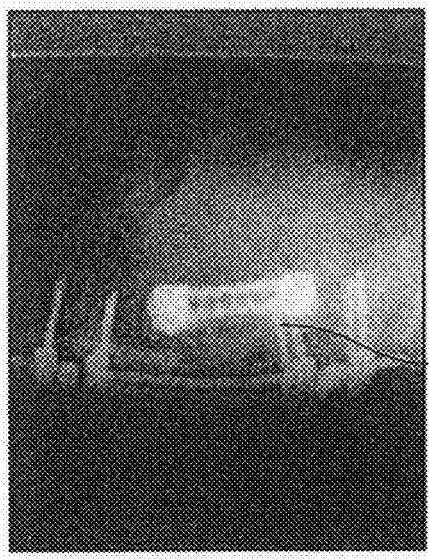
Figure 32:
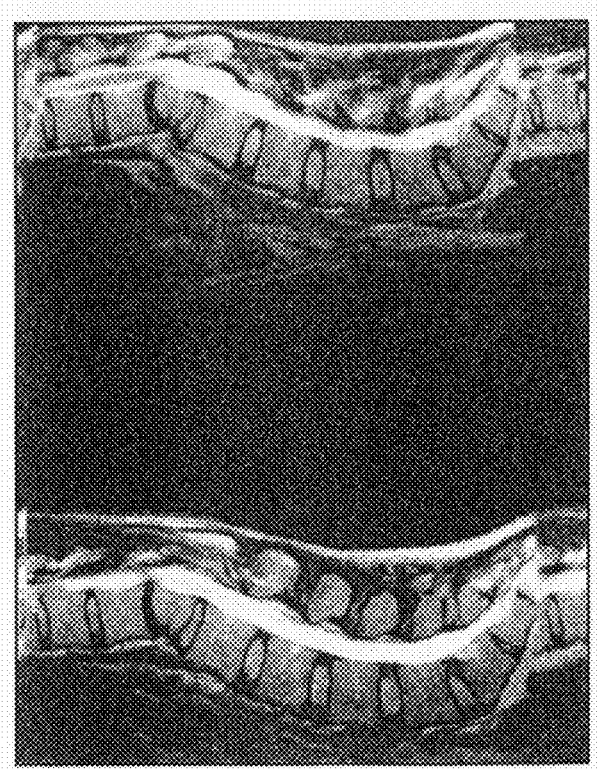
Figure 37:
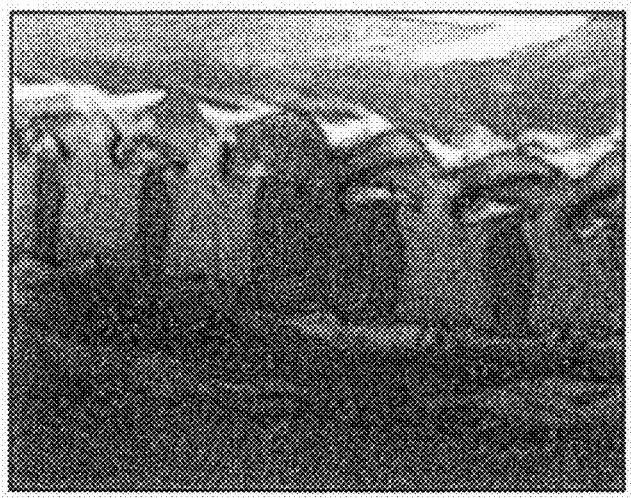
Figure 36:
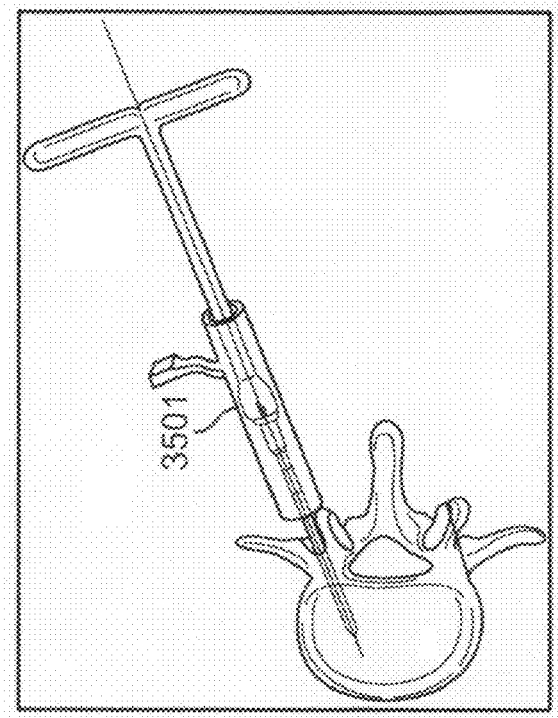
Figure 35:
Figure 39:
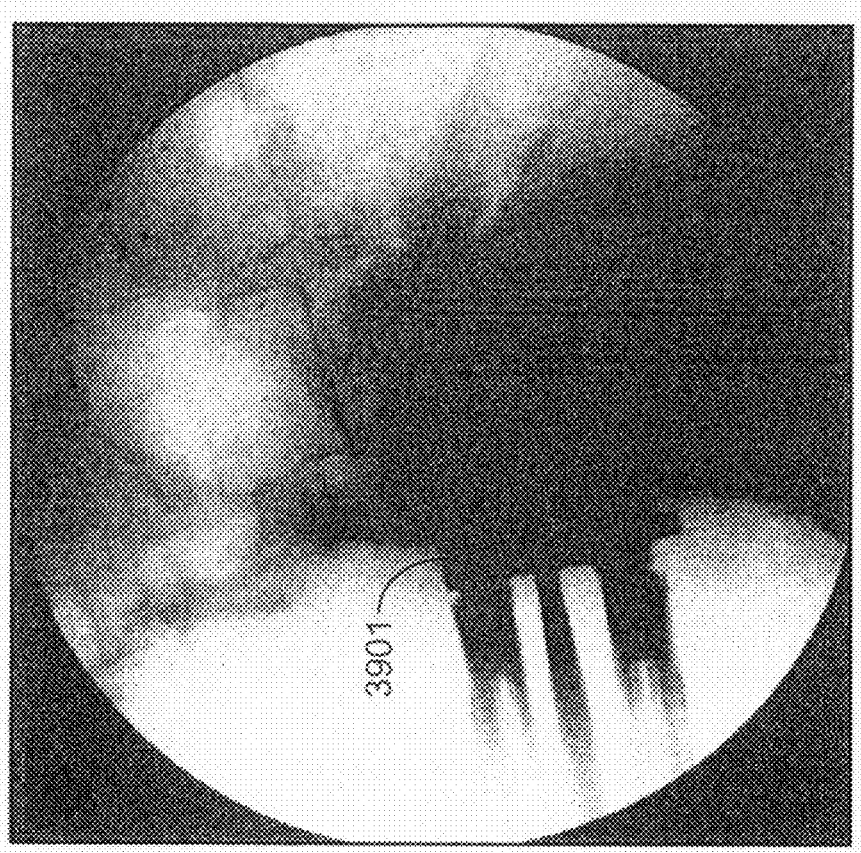
Figure 38:
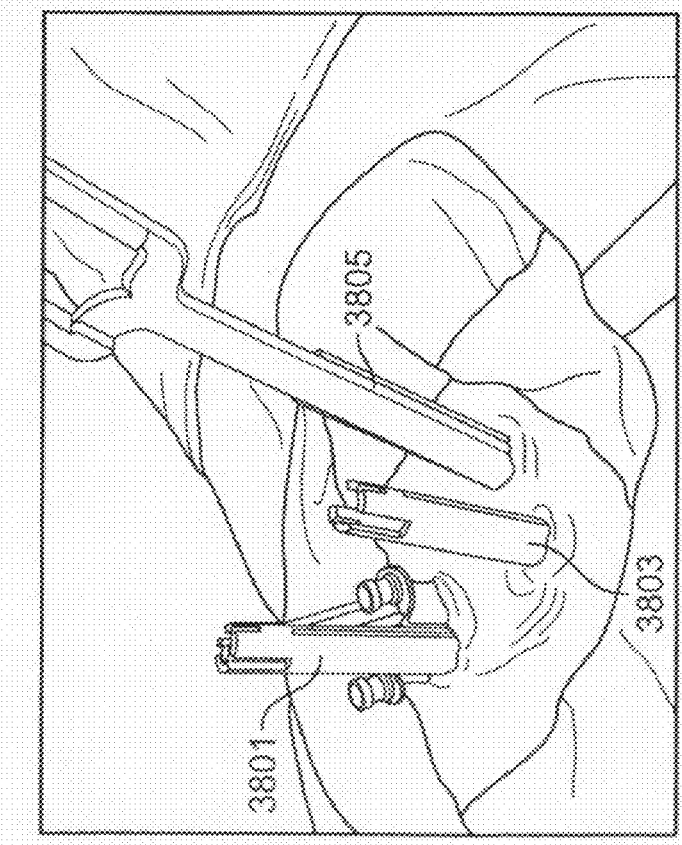

Various case examples of instrumented spine surgery to which the presently disclosed technology may be applied for the benefit of spinal patients suffering from a variety of spinal diseases, degenerative conditions and diseases, are shown in FIGS. 26-39. A spinal implant 2601 is shown via FIGS. 26, 27 and 28, such implant having been implanted for the benefit of a patient afflicted with an L2/3 listhesis. A spinal implant 2901 is shown via FIGS. 29, 30 and 31, such implant having been implanted for the benefit of a patient that suffered an L2 burst fracture. A patient suffering from an L1 burst, including progressive Kyphosis, pain and paraparesis, may benefit from implantation of a spinal implant 3201, as shown in FIGS. 32, 33 and 34. A patient diagnosed with metastatic bone disease may be treated with spinal surgical apparatus 3501, as shown in FIGS. 35, 36 and 37. Images of spinal surgical apparatus 3801, 3803 and 3805, and an associated spinal implant 3901, are shown in FIGS. 38 and 39 (in which an example of minimally invasive surgery is illustrated). As discussed, the presently disclosed technology may be employed in conjunction with such spinal implant applications, as well as spinal implant applications similar thereto.

Figure 40:
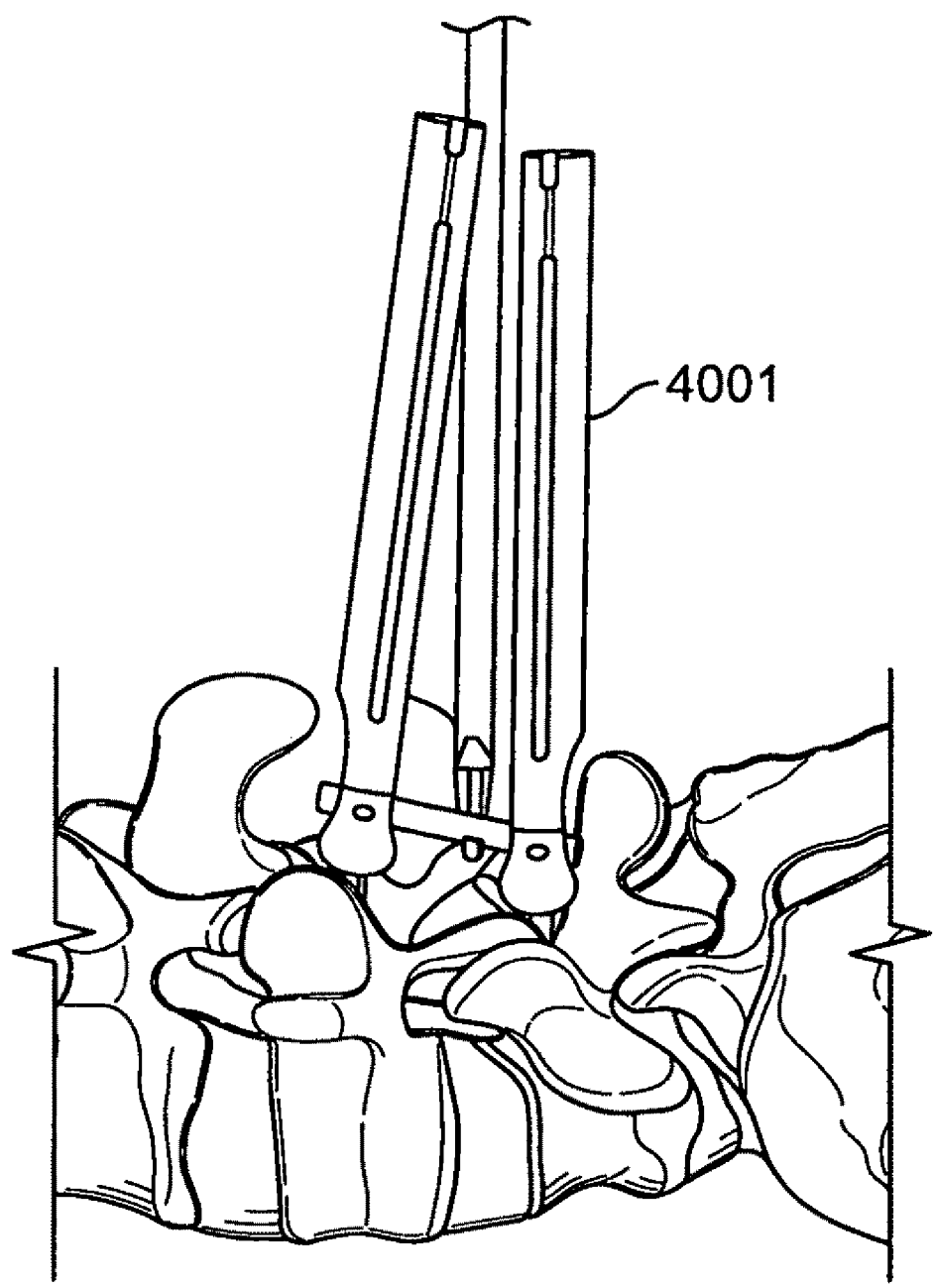
FIGS. 40 and 41 illustrate existing technology for intraoperative location of breaches in the cortical bone tissue of spinal pedicles.
Figure 41:
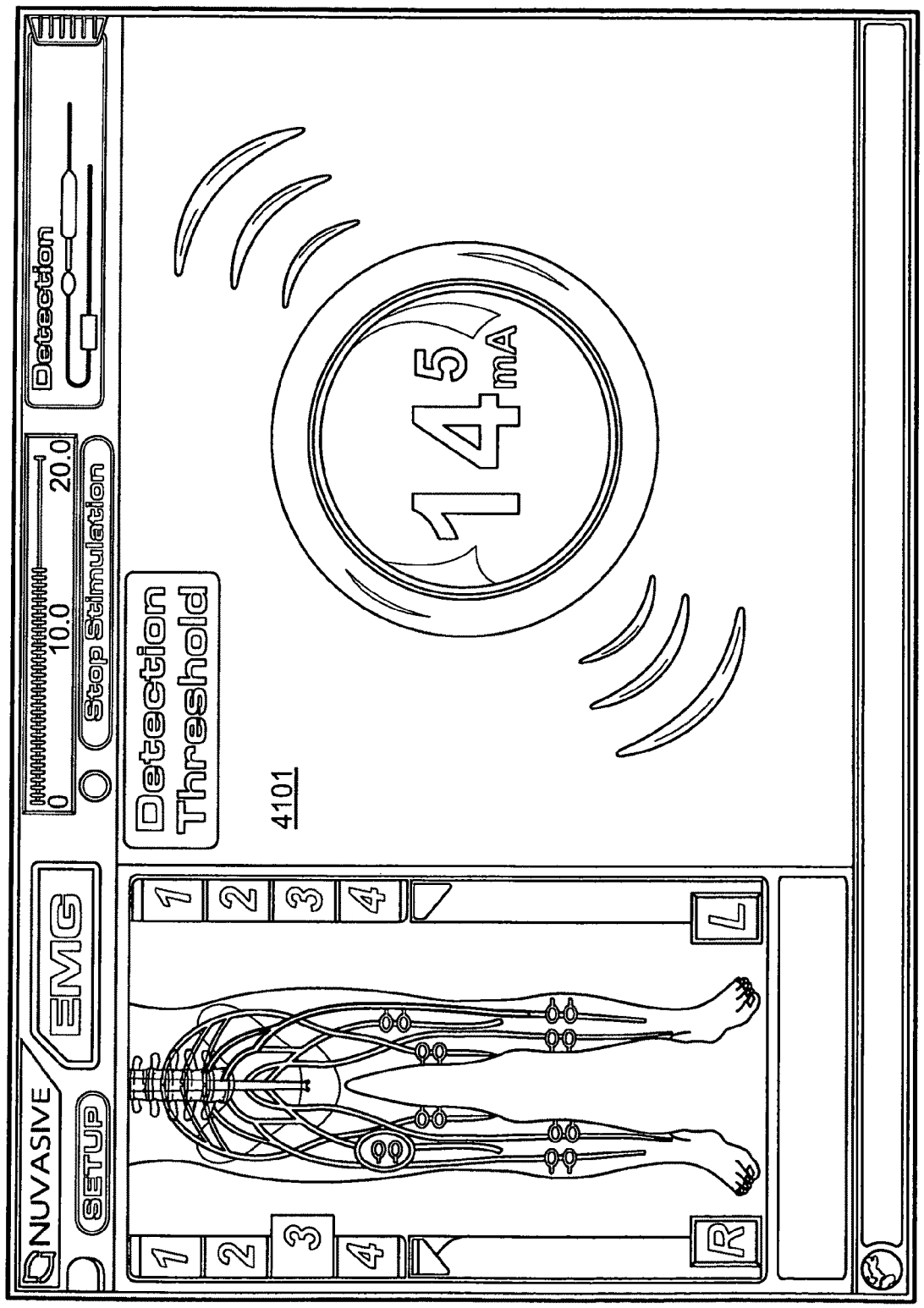

Referring now to FIGS. 40 and 41, existing technology for locating breaches in the cortical bone tissue of spinal pedicles is depicted. More particularly, diagnostic apparatus such as the apparatus 4001 may be used with integrated display technology (such as a screen display 4101) to implement a scheme for intraoperative monitoring of electrical current with respect to a predetermined threshold, wherein observed current in excess of the predetermined threshold is taken as a strong indication of the presence of an inappropriate cortical breach. However, the systems, apparatus and methods of the present disclosure offer superior results and clinical benefits as compared to such prior art technology.

Figure 43:
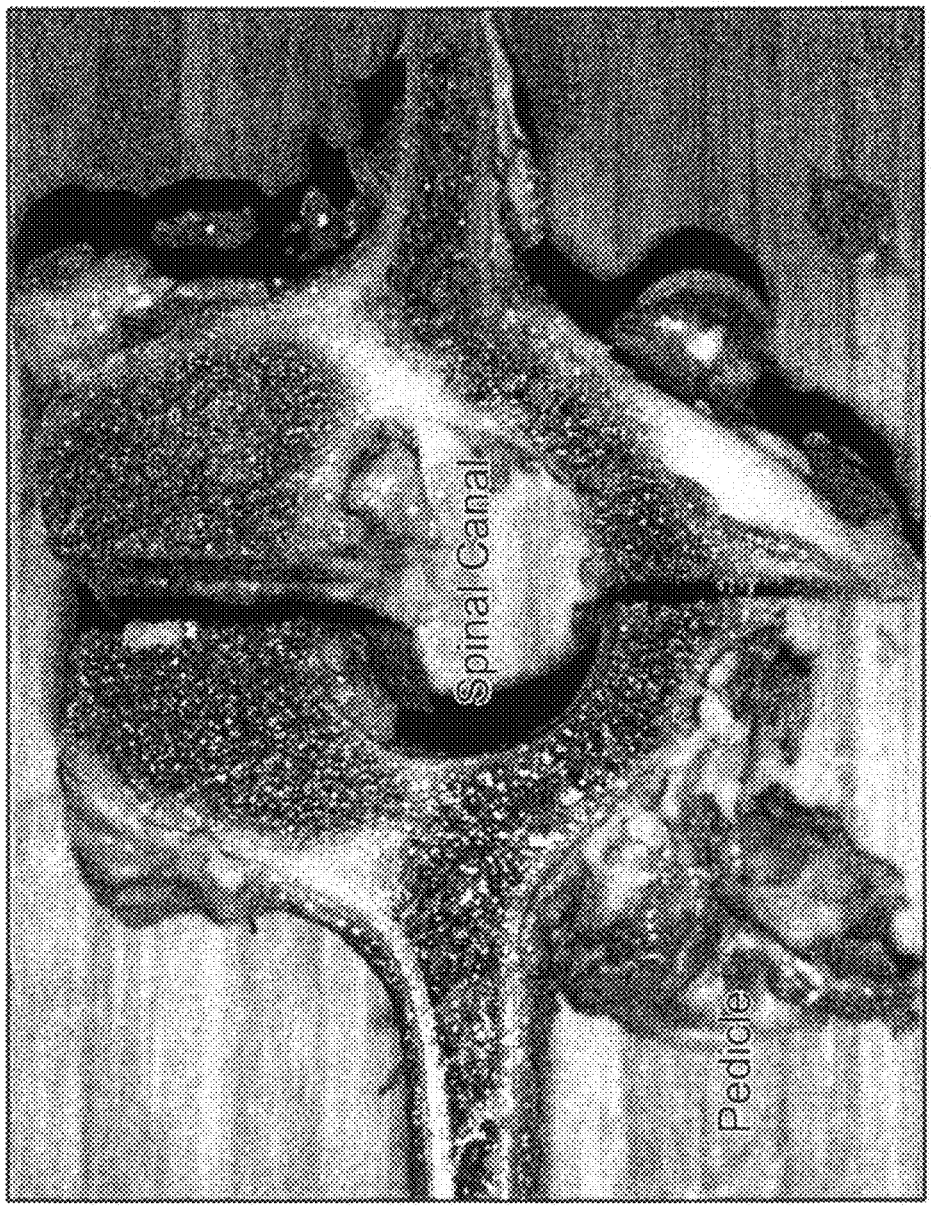
Figure 45:
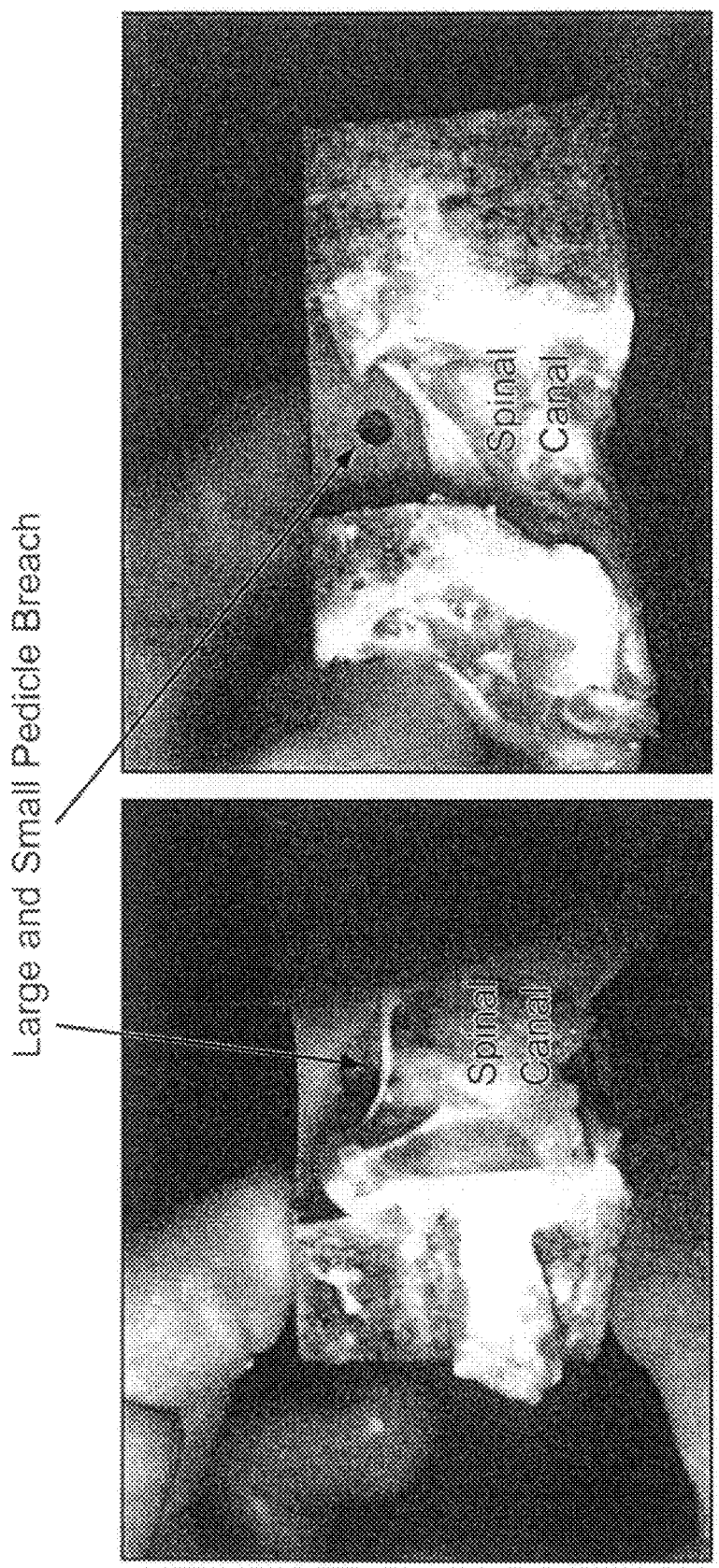
Figure 47:
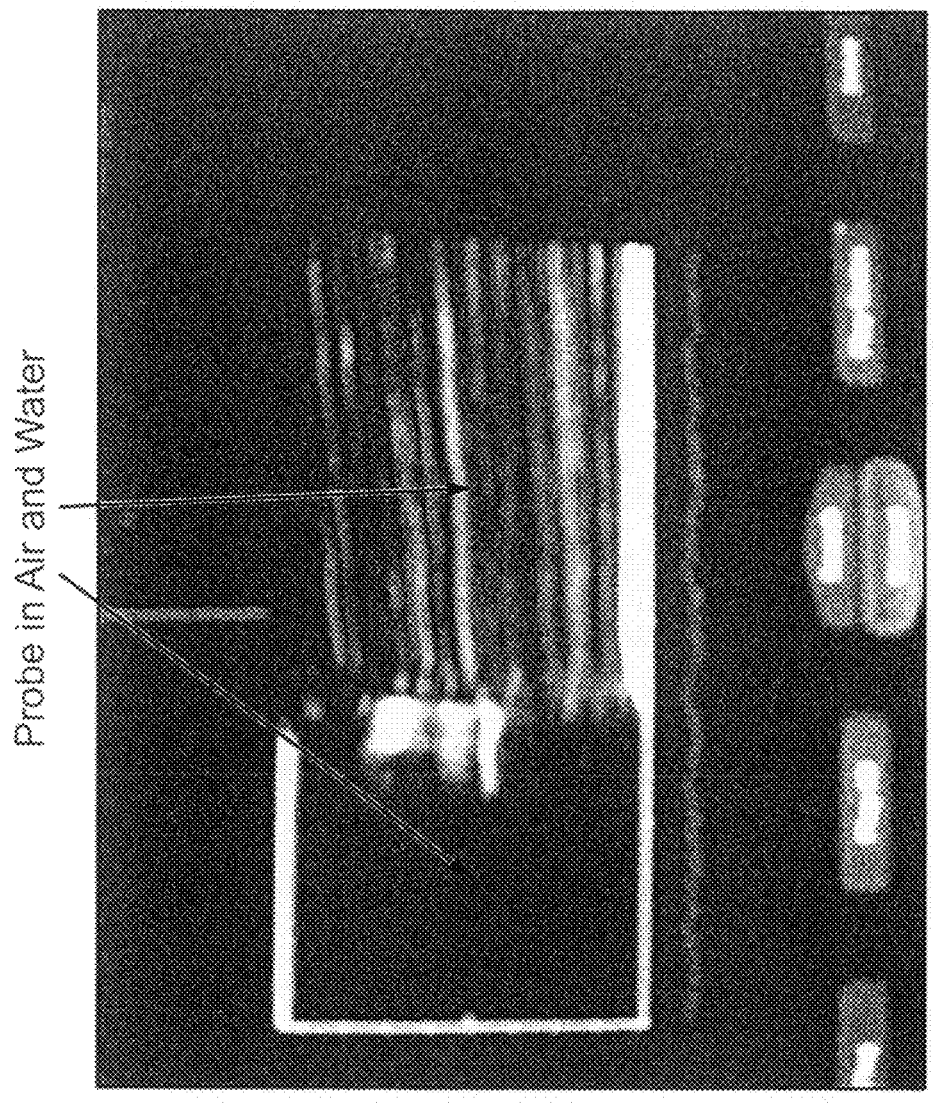
Figure 49:
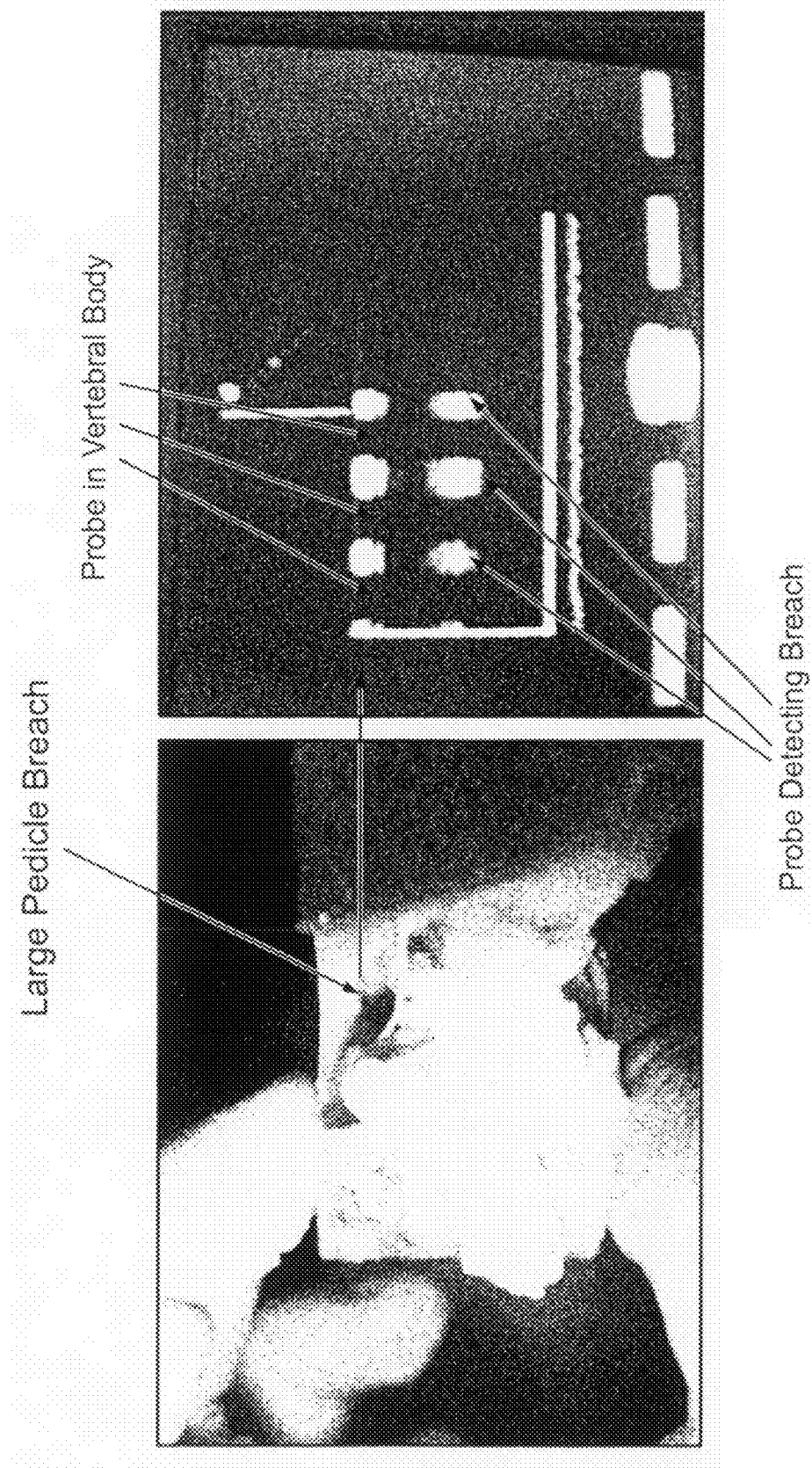
Figure 50:
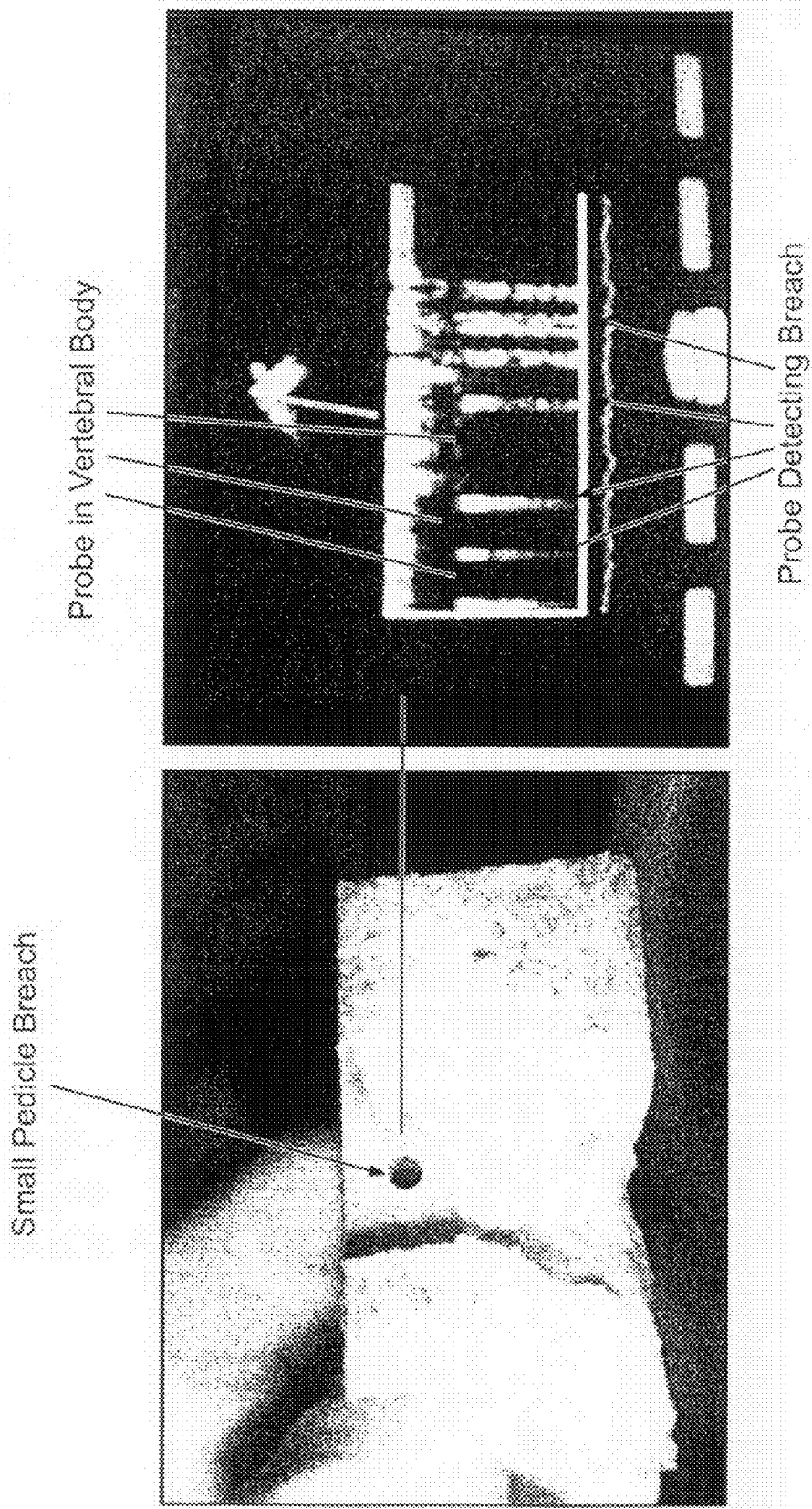

Referring now to information shown and described in FIGS. 42-50, tests have been performed with respect to animal vertebral bodies using a 2.7 mm diameter ultrasound probe in accordance with embodiments of the present disclosure. Associated test materials are shown in FIG. 42, relevant anatomy is shown in FIG. 43, and associated testing methods are illustrated in FIG. 44. Large and small pedicle breaches are exemplified in images encompassed by FIG. 45. Examples of test materials presenting an intact pedicle (i.e., a pedicle having no breach in the side walls of the pedicle entry hole such as would result in the pedicle entry hole communicating with the spinal canal) are shown in images encompassed by FIG. 46. Examples of experimental controls, including with respect to the response of the probe in air and water, are shown in FIG. 47. The images of FIG. 48 show that no applicable signal was detected with the test probe in the example of an intact pedicle with no breach. As shown in FIG. 49, employment of the test probe in conjunction with test materials in which a large pedicle breach was present resulted in the test probe detecting such large breach. As shown in FIG. 50, employment of the test probe in conjunction with test materials in which a small pedicle breach was present resulted in the test probe detecting such small breach.

Figure 51:
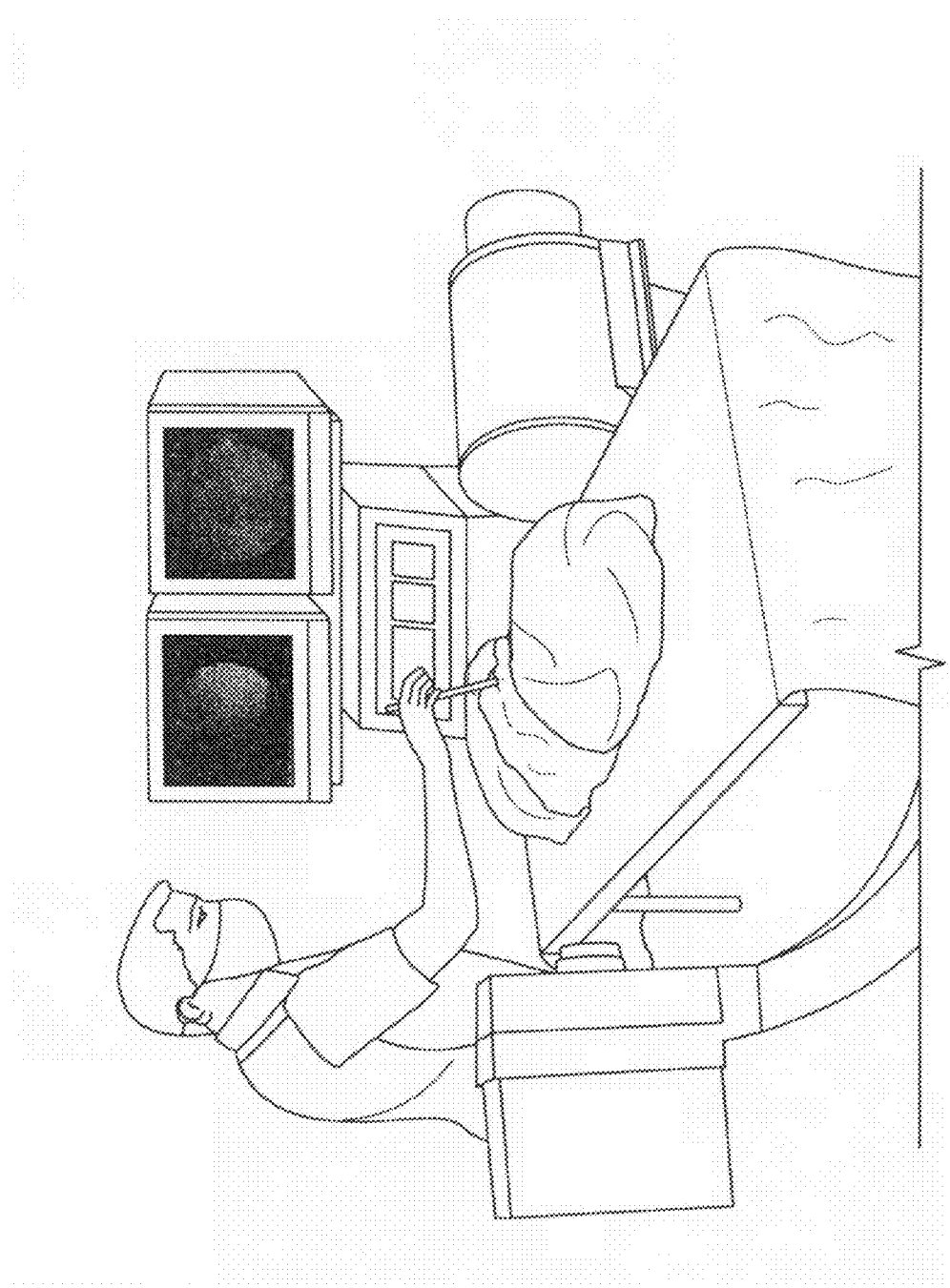
Figure 52:
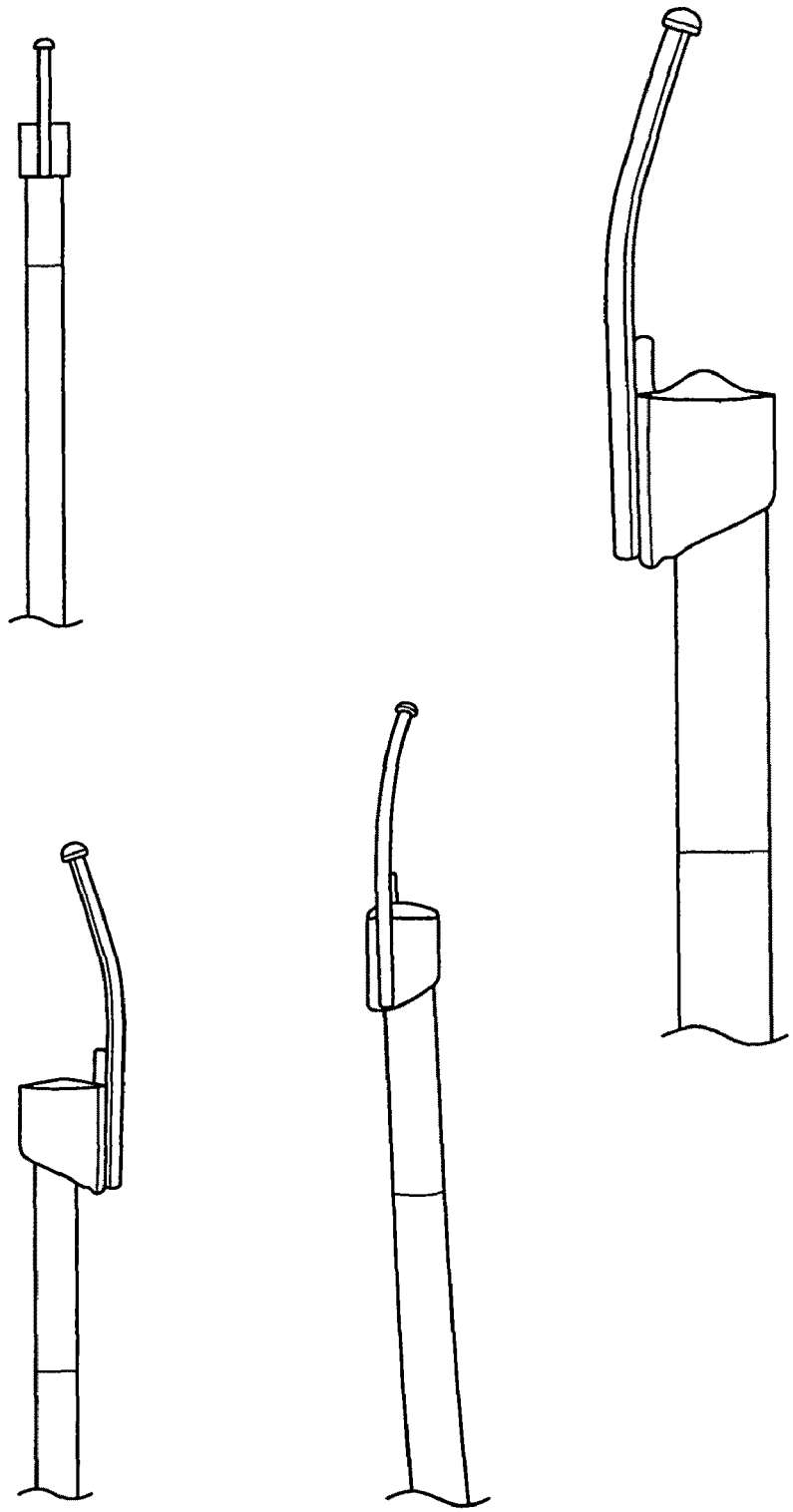
Figure 53:
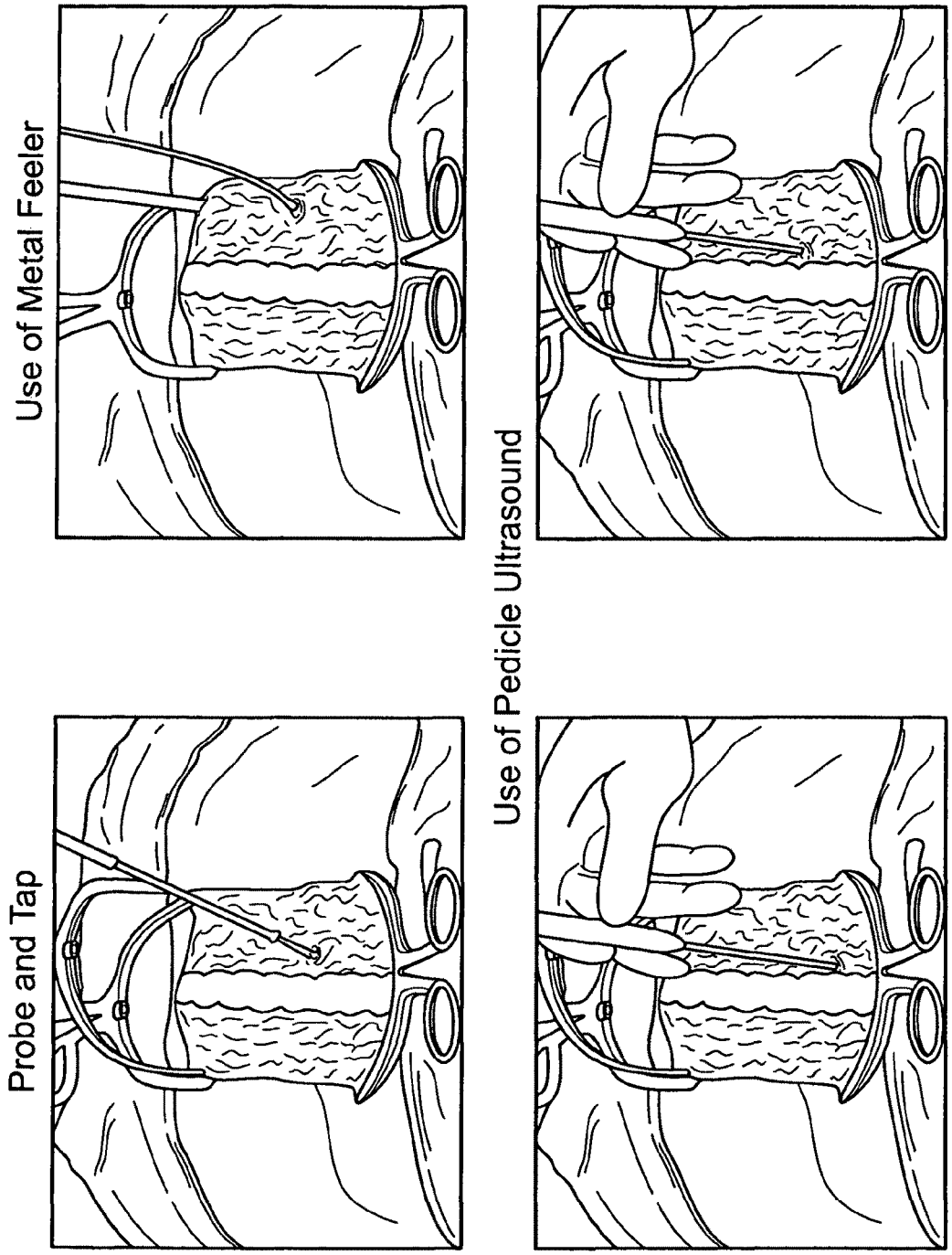
Figure 55:
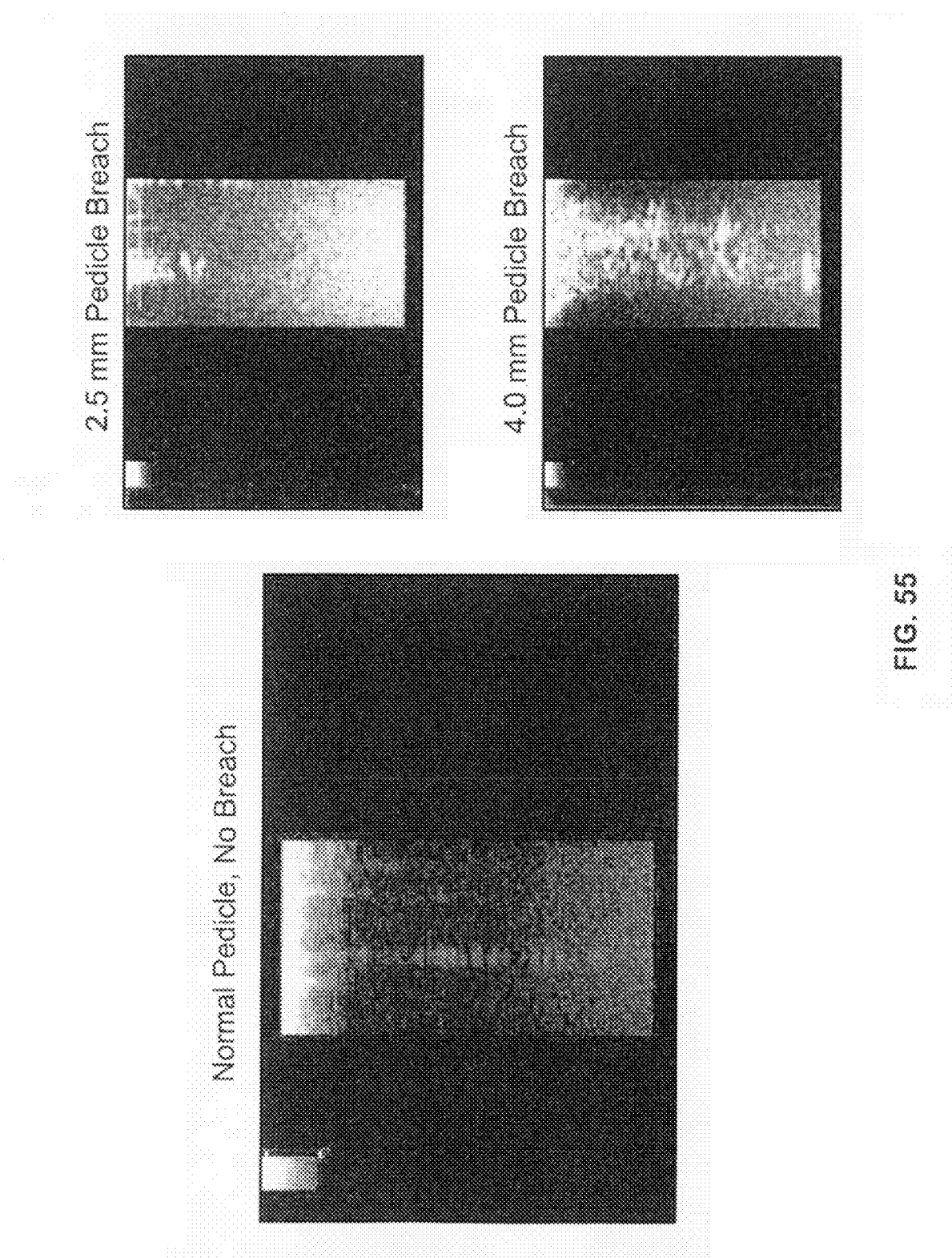

Referring now to information shown and described in FIGS. 51-55, further tests have been conducted with respect to human cadaveric subjects. FIG. 51 illustrates a related test setup. As shown in images encompassed by FIG. 52, the tests included the use of a 3.18 mm side-firing ultrasound probe fitted with a detachable pedicle feeler/sounder in accordance with the present disclosure. Various methods and techniques associated with the human cadaveric tests are shown in the images encompassed by FIG. 53. Some results corresponding to data collected and compared for a metal pedicle feeler (top) versus the use of pedicle ultrasound in accordance with the techniques and apparatus of the present disclosure are shown in the images encompassed by FIG. 54. Further results exemplifying the diagnostic power of the techniques and apparatus of the present disclosure, are shown in the images encompassed by FIG. 55 and corresponding respectively to: 1) a normal pedicle with no breach, 2) a 2.5 mm pedicle breach, and 3) a 4.0 mm pedicle breach.

Test results with respect to 2.5 mm and 4.0 mm pedicle breaches and related explanatory information are set forth in the following tables. For purposes of the tables, the following terms are defined:

Sensitivity=(# true pos.)/[(# true pos.)+(# false neg.)]

Specificity=(# true neg.)/[(# true neg.)+(# false pos.)]

Positive Predictive Value (PPV)=(# true pos.)/[(# true pos.)+(# false pos.)]

Negative Predictive Value (NPV)=(# true neg.)/[(# true neg.)+(# false neg.)]

TABLE 1

Test Results; 2.5 mm Pedicle Breach

| | Pedicle Feeler | Pedicle Ultrasound #1 | Pedicle Ultrasound #2 |
|---|---|---|---|
| Sensitivity | 66.7% | 85.7% | 85.7% |
| Specificity | 80% | 80% | 80% |
| PPV | 85.7% | 85.7% | 85.7% |
| NPV | 57% | 80% | 80% |

TABLE 2

Test Results; 4.0 mm Pedicle Breach

| | Pedicle Feeler | Pedicle Ultrasound #1 | Pedicle Ultrasound #2 |
|---|---|---|---|
| Sensitivity | 85.7% | 100% | 100% |
| Specificity | 100% | 100% | 100% |
| PPV | 100% | 100% | 100% |
| NPV | 80% | 100% | 100% |

Based on the foregoing test results, including specifically the noted human cadaveric tests, the following conclusions have been reached:

- The disclosed apparatus, systems and methods (pedicle ultrasound) has a higher sensitivity and negative predictive value as compared to the "classic" pedicle feeler.
- The noted difference is greater with extremely small breaches (2.5 mm vs. 4.0 mm)
- With larger breaches (4.0 mm), the detection of breaches approaches a sensitivity and specificity of 100% using the pedicle ultrasound system.
- The disclosed apparatus, systems and methods facilitate screening tests and/or related diagnostics to determine/detect whether a breach in cortical bone has occurred when placing pedicle screws into the spine.
- The disclosed apparatus, systems and methods allow surgeons and other health care personnel to reduce the likelihood that pedicle screws will be misplaced in spinal surgery, thereby translating to more effective health care.

Figure 56:
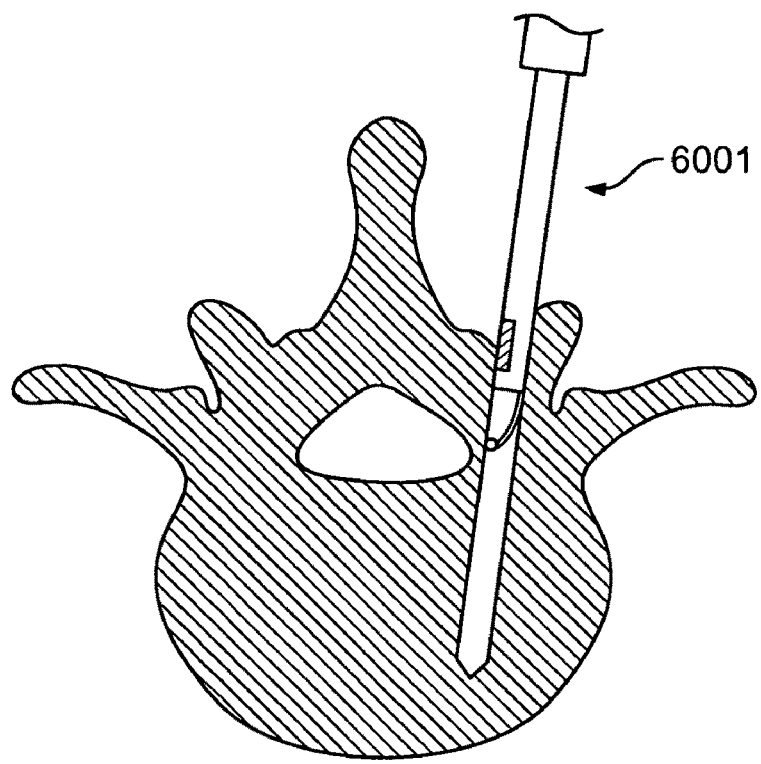
FIGS. 56-57 are successive views of a medical diagnostic instrument in accordance with the present disclosure being used in vivo to locate potential pilot hole bone tissue defects prior to pedicle screw implantation.
Figure 57:
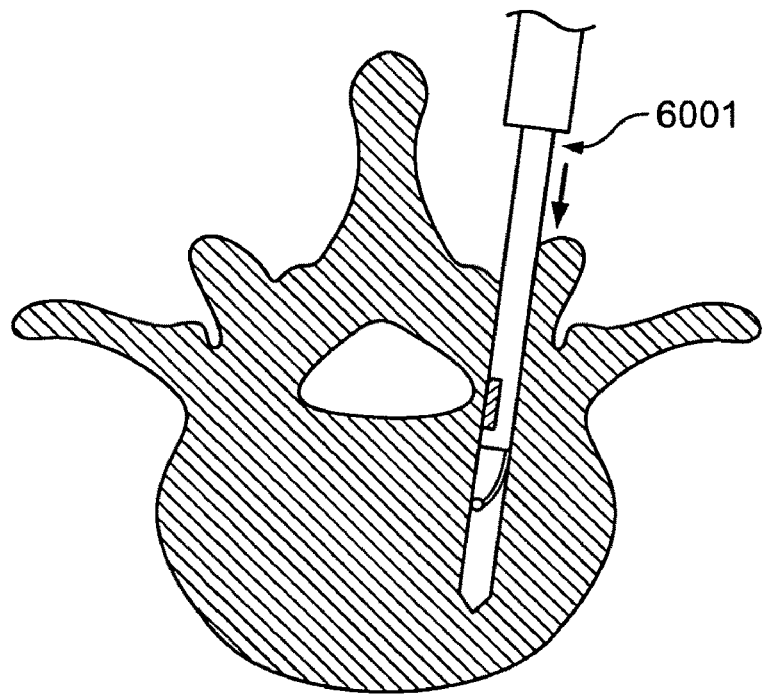

In operation, and as illustrated in FIGS. 56 and 57, the above described diagnostic instruments may be used to explore a pedicle screw pilot hole formed in the spine of a human patient for cortical breaches located in the axially-extending side-walls thereof. As shown in FIGS. 56 and 57, a medical diagnostic instrument 6001 in accordance with the present disclosure is presented. The instrument includes a handle, an ultrasound probe, and a tactile feeler probe. The ultrasound probe includes a longitudinal shaft extending distally from the handle and terminating in a distal end, and an ultrasound transducer mounted to the longitudinal shaft proximate the distal end thereof. The ultrasound transducer includes an array of side-firing ultrasonic energy generation elements extending along the longitudinal shaft.

The tactile feeler probe is mounted with respect to the ultrasound probe and includes a longitudinal shaft mounted with respect to the longitudinal shaft of the ultrasound probe and extending distally therefrom beyond the distal end thereof. The tactile feeler probe includes a feeler probe tip defined at a distal end of the longitudinal shaft of the tactile feeler probe.

The handle is employed to manually grasp and manipulate the medical diagnostic instrument relative to the spine of a human patient, including inserting the ultrasound transducer and the distal end of the longitudinal shaft of the ultrasound probe, and the feeler probe tip and the longitudinal shaft of the tactile feeler probe into a pedicle screw pilot hole formed in the spine of the human patient.

The feeler probe tip of the tactile feeler probe is positioned relative to a selected portion of the side wall of the pedicle screw pilot hole such that the feeler probe tip is positioned against the side wall of the pedicle screw pilot hole.

The feeler probe tip of the tactile feeler probe is employed to perform a tactile inspection of the selected portion of the side wall for purposes of detecting manually-detectable cortical breaches located therein.

The array of side-firing ultrasonic energy generation elements of the ultrasound transducer are positioned relative to selected portion of a side wall of the pedicle screw pilot hole such that the array of side-firing ultrasonic energy generation elements extends axially along, and is positioned against, the selected portion of a side wall of the pedicle screw pilot hole.

The array of side-firing ultrasonic energy generation elements of the ultrasound transducer is employed to obtain a two-dimensional image of the selected portion of the side wall for visual inspection for purposes of detecting ultrasonically-detectable cortical breaches located therein.

The two positioning and the two array employment steps are performed without removing any of the ultrasound transducer or the distal end of the longitudinal shaft of the tactile feeler probe or the feeler probe tip of the longitudinal shaft of the tactile feeler probe from the pedicle screw pilot hole.

The instrument may be mounted and slid along a K-wire (not specifically shown) to guide the ultrasound and tactile feeler probes axially relative to the pedicle screw pilot hole during a minimally invasive surgical procedure. Alternatively, and/or in addition, the instrument may be mounted with respect to one or more guide wires other than a K-wire.

Figure 58:
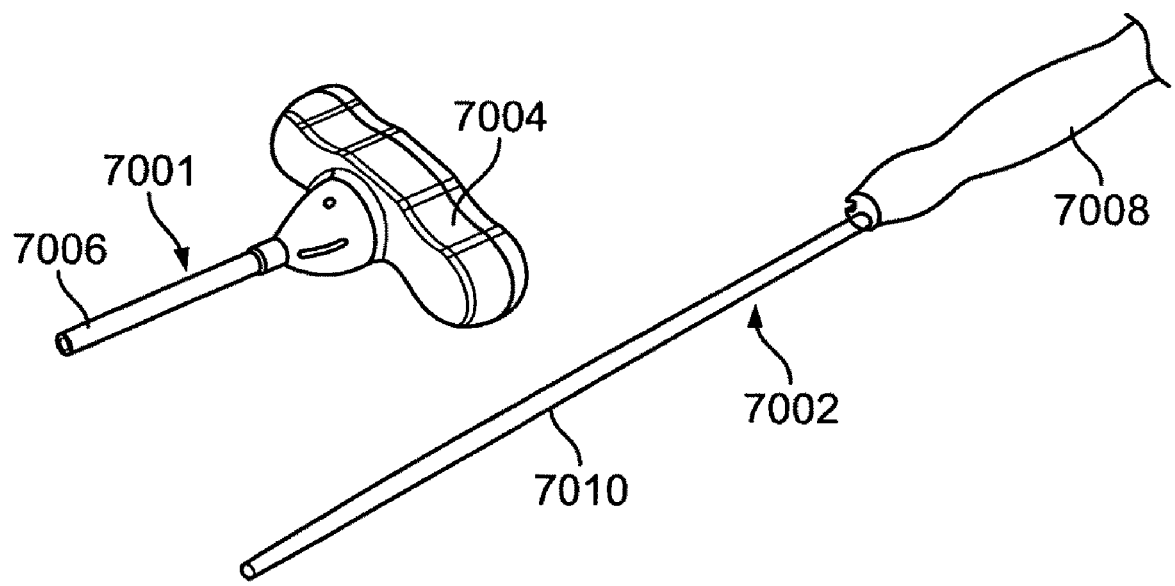
FIGS. 58-59 are views of an implementation according to the present disclosure wherein a modified Jamshidi-style needle is used in combination with an ultrasound probe.
Figure 59:
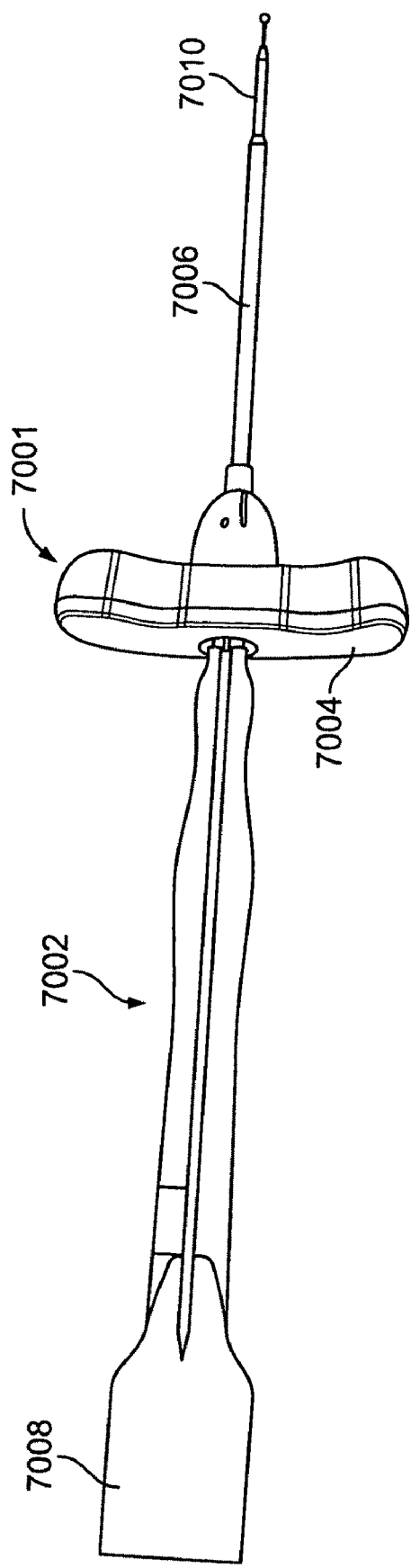

With reference to FIGS. 58-59, a further implementation according to the present disclosure is shown. Thus, a modified Jamshidi-style needle assembly 7001 may be employed with an ultrasound probe assembly in clinical applications, e.g., to detect/determine a breach in the cortical bone associated with pedicle screw placement. The Jamshidi-style needle assembly 7001 generally takes the form of a long hollow needle 7006 with a tapered cutting edge at a distal end thereof. A handle 7004 is mounted with respect to the needle 7006 and defines an aperture for receipt of an inner needle (not pictured) and ancillary element(s). In conventional use of a Jamshidi-style needle, the inner needle may be removed once a desired anatomical location is reached and a syringe may be introduced through the aperture formed in the handle for use in sampling tissue, e.g., bone marrow. However, in the exemplary implementation disclosed herein, after removal of the inner needle (not pictured), the aperture formed in handle 7004 of Jamshidi-style needle assembly 7001 is configured and dimensioned to receive an elongated ultrasound probe 7010 associated with ultrasound assembly 7002. In exemplary implementations, the ultrasound assembly 7002 includes a handle member 7008 that defines a fitting for connection to conventional cabling.

In use, the Jamshidi-style needle assembly 7001 is introduced to a desired clinical location, e.g., within cortical bone that has been pre-drilled for receipt of a pedicle screw, and the inner needle (not pictured) is removed. Ultrasound probe 7010 is then introduced through the aperture formed in the handle 7004 of the Jamshidi-style needle assembly 7001 for advantageous ultrasound detection of relevant information, e.g., a breach of the cortical bone. In exemplary implementations, needle 7006 is approximately 7.5 cm in length and the inner diameter of needle 7006 is approximately 3 mm. Alternative dimensions may be employed without departing from the spirit or scope of the present disclosure.

Although the systems, apparatus and methods have been described with respect to exemplary embodiments herein, it is apparent that modifications, variations, changes and/or enhancements may be made thereto without departing from the spirit or scope of the invention as defined by the appended claims. For example, as an alternative to the use of a side-firing ultrasound transducer as described hereinabove, and/or in addition thereto, one or more end-firing ultrasound transducers, and/or 360 degree ultrasound transducers may be employed, whether mounted with respect to the distal end of the longitudinal shaft of the associated ultrasound probe, adjacent thereto, or otherwise, for use as desired by the surgical practitioner. Ultrasound probes and systems in accordance with the present disclosure may employ or embody one or more of a variety of modes of ultrasound, including but not necessarily limited to Ultrasound Mode A, Ultrasound Mode B, Ultrasound Mode M, Ultrasound DM Mode, as well as color and three-dimensional modes. Other instruments may be modularly attached in addition to, and/or in place of a tactile feeler probe, including but not limited to curettes, nerve hooks, Woodsons, and/or Murphey Balls. Accordingly, the present disclosure expressly encompasses all such modifications, variations, changes and/or enhancements.

The invention claimed is:

1. A medical diagnostic instrument, comprising:
a proximal handle configured and dimensioned to permit an operator to manually grasp the instrument;
an ultrasound probe including a longitudinal shaft extending distally from the handle and terminating in a distal end, and an ultrasound transducer mounted with respect to the longitudinal shaft, the ultrasound transducer including an array of ultrasonic energy generation elements; and
a tactile feeler probe mounted with respect to the ultrasound probe;
at least one hollow receiver member mounted with respect to the longitudinal shaft of the ultrasound probe;
wherein the ultrasound transducer and the distal end are cooperatively configured, oriented, and dimensioned to permit the operator to insert the ultrasound transducer and the distal end into a desired anatomical location to permit the operator to obtain thereat a corresponding two-dimensional image of the anatomical location for visual inspection by the operator for purposes of detecting ultrasonically-detectable anatomical properties;
wherein the at least one hollow receiver member is configured and dimensioned to receive a K-wire to permit the instrument to be slidably mounted thereto for purposes of guiding the ultrasound and tactile feeler probes axially relative to the desired anatomical location;
wherein the tactile feeler probe is configured and dimensioned to permit the operator to insert the tactile feeler probe into the desired anatomical location to permit the operator to perform thereat a tactile inspection of the selected anatomical location.

2. The medical diagnostic instrument of claim 1, wherein the tactile feeler probe further Comprises a longitudinal shaft mounted with respect to the longitudinal shaft of the ultrasound probe and extends distally beyond the distal end thereof, and a feeler probe tip defined at a distal end of the longitudinal shaft of the tactile feeler probe; and
wherein the feeler probe tip and the longitudinal shaft of the tactile feeler probe are cooperatively configured and dimensioned to permit the operator to insert the feeler probe tip and the longitudinal shaft of the tactile feeler probe into the desired anatomical location to permit the operator to perform thereat a tactile inspection of the selected anatomical location.

3. The medical diagnostic instrument of claim 1, wherein the desired anatomical location is a pedicle screw pilot hole formed in the spine of the human patient, and wherein the array of ultrasonic energy generation elements of the ultrasound transducer extends axially along, and is positioned against, a selected portion of a side wall of the pedicle screw pilot hole.

4. The medical diagnostic instrument of claim 2, wherein the longitudinal shaft of the tactile feeler probe defines at least a first longitudinal axis along which the longitudinal shaft of the tactile feeler probe extends distally from the longitudinal shaft of the ultrasound probe, at least a second longitudinal axis along which the longitudinal shaft of the tactile feeler probe extends distally to the feeler probe tip, and a bend formed therebetween such that the first and second longitudinal axes collectively define a first plane.

5. The medical diagnostic instrument of claim 4, wherein the longitudinal shaft of the ultrasound probe defines at least a third longitudinal axis along which the longitudinal shaft of the ultrasound probe extends distally from the handle, wherein the ultrasonic energy generation elements of the array thereof define a fourth longitudinal axis along which the array of ultrasonic energy generation elements extends, wherein the fourth longitudinal axis is radially offset from the third longitudinal axis such that the third and fourth longitudinal axes collectively define a second plane, and wherein the second plane is coplanar with the first plane.

6. The medical diagnostic instrument of claim 5, wherein each of the feeler probe tip and the fourth longitudinal axis is offset from the third longitudinal axis in a common radial direction therefrom such that the feeler probe tip and the array of ultrasonic energy generation elements are rotationally aligned with each other relative to the longitudinal shaft of the ultrasound probe.

7. The medical diagnostic instrument of claim 2, wherein the longitudinal shaft of the ultrasound probe defines a first longitudinal axis along which the longitudinal shaft of the ultrasound probe extends distally from the handle, wherein the ultrasonic energy generation elements of the array thereof define a second longitudinal axis along which the array of ultrasonic energy generation elements extends, wherein the second longitudinal axis is at least partially disposed in radially spaced relation with respect to the first longitudinal axis such that the first and second longitudinal axes collectively define a first plane, and wherein the feeler probe tip is disposed in the first plane.

8. The medical diagnostic instrument of claim 1, wherein the longitudinal shaft of the ultrasound probe defines a first longitudinal axis along which the longitudinal shaft of the ultrasound probe extends distally from the handle, wherein the ultrasonic energy generation elements of the array thereof define a second longitudinal axis along which the array of ultrasonic energy generation elements extends, wherein the second longitudinal axis is radially offset from the first longitudinal axis such that the first and second longitudinal axes define a first plane, wherein the handle includes a longitudinal shaft extending proximally from the ultrasound probe and terminating in a proximal end, the longitudinal shaft of the handle defining a third longitudinal axis along which the handle extends proximally from the ultrasound probe, the third longitudinal axis being disposed in the first plane.

9. The medical diagnostic instrument of claim 1, further comprising at least one channel configured and dimensioned to receive the K-wire to permit the instrument to be slidably mounted thereto for purposes of guiding the ultrasound and tactile feeler probes axially relative to the desired anatomical location, the channel being one of formed in the handle and extending therethrough, and formed in an extension of the handle and extending therepast.

10. The medical diagnostic instrument of claim 8, wherein the longitudinal shaft of the handle further defines a fourth longitudinal axis disposed in the first plane and along which the longitudinal shaft of the handle extends proximally to the proximal end of the handle, and a bend formed between the third and fourth longitudinal axes such that an angle defined between the fourth and first longitudinal axes is larger than an angle defined between the third and first longitudinal axes, and such that the handle functions as a bayonet handle relative to the ultrasound and feeler probes.

11. The medical diagnostic instrument of claim 1, wherein the handle includes a housing, and wherein the ultrasound probe is mounted with respect to the handle such that the longitudinal shaft of the ultrasound probe is supported, cantilever-style, by the handle housing.

12. The medical diagnostic instrument of claim 2, wherein the tactile feeler probe is mounted with respect to the ultrasound probe such that the longitudinal shaft of the tactile feeler probe is supported, cantilever-style, by the longitudinal shaft of the ultrasound probe.

13. The medical diagnostic instrument of claim 1, wherein the array of ultrasonic, energy generation elements is side-firing and is one of a linear array and a phased array.

14. The medical diagnostic instrument of claim 1, further comprising a cable assembly for carrying electrical signals to and from the ultrasound transducer in accordance with an ultrasonic imaging mode of use of the instrument, the cable assembly including a proximal end including an electrical connector for connecting the instrument to a corresponding ultrasound console and current carrying wires extending distally from the electrical connector to the ultrasound transducer at least partially via a corresponding interior conduit formed in and extending longitudinally along the longitudinal shaft of the ultrasound probe; and
    wherein the handle includes a longitudinal shaft extending proximally from the ultrasound probe and terminating in a proximal end, wherein the current carrying wires extend to the ultrasound transducer through the proximal end of the handle and through a corresponding interior conduit formed in and extending longitudinally along the longitudinal shaft of the handle.

15. The medical diagnostic instrument of claim 1, wherein the array of ultrasonic energy generation elements defines an axial length along the longitudinal shaft of the ultrasound probe of between about 8 millimeters and about 12 millimeters; and
    wherein the tactile feeler probe extending distally beyond the distal end of the longitudinal shaft of the ultrasound probe includes wherein the longitudinal shaft and the feeler probe tip of the tactile feeler probe collectively define an axial length of the tactile feeler probe beyond the array of side-firing ultrasonic energy generation elements of between about 8 millimeters and about 12 millimeters.

16. The medical diagnostic instrument of claim 9, wherein the at least one hollow receiver member is mounted with respect to a distal portion of the longitudinal shaft of the ultrasound probe;
    and wherein the channel defines at least a first longitudinal axis and the at least one hollow receiver member defines at least a second longitudinal axis, the first and second longitudinal axes being substantially aligned with one another.

17. The medical diagnostic instrument of claim 1, wherein the at least one hollow receiver member comprises a first hollow receiver member and a second hollow receiver member mounted with respect to the longitudinal shaft of the ultrasound probe, each hollow receiver member configured and dimensioned to receive the K-wire to permit the instrument to be slidably mounted thereto for purposes of guiding the ultrasound and tactile feeler probes axially relative to the desired anatomical location;
    wherein the first hollow receiver member is mounted with respect to a distal portion of the longitudinal shaft of the ultrasound probe and the second hollow receiver member is mounted with respect to a proximal end of the ultrasound probe.

18. The medical diagnostic instrument of claim 17, wherein at least a portion of the second hollow receiver member is mounted with respect to the handle.

19. The medical diagnostic instrument of claim 1, wherein the at least one hollow receiver member extends from a distal portion of the longitudinal shaft of the ultrasound probe to a proximal end of the ultrasound probe.

20. The medical diagnostic instrument of claim 19, wherein at least a portion of the at least one hollow receiver member is mounted with respect to the handle.

21. A medical diagnostic system for use in conjunction with bone tissue, comprising:
    a medical diagnostic instrument, the instrument including:
        a handle, the handle being disposable proximate an operator of the instrument, the handle being further configured and dimensioned to permit the operator to manually grasp the instrument and manipulate the instrument relative to the spine of a human patient;
        an ultrasound probe, the ultrasound probe including a longitudinal shaft extending distally from the handle and terminating in a distal end, and an ultrasound transducer mounted to the longitudinal shaft proximate the distal end thereof, the ultrasound transducer including an array of side-firing ultrasonic energy generation elements extending along the longitudinal shaft, wherein the ultrasound transducer and the distal end are cooperatively configured, oriented, and dimensioned to permit the operator to insert the ultrasound transducer and the distal end into a pedicle screw pilot hole formed in the spine of the human patient such that the array of side-firing ultrasonic energy generation elements of the ultrasound transducer extends axially along, and is positioned against, a selected portion of a side wall of the pedicle screw pilot hole, and to permit the operator to obtain thereat a corresponding two-dimensional image of the selected portion of the side wall for visual inspection by the operator for purposes of detecting ultrasonically-detectable cortical breaches located therein;
        a tactile feeler probe mounted with respect to the ultrasound probe, the tactile feeler probe including a longitudinal shaft mounted with respect to the longitudinal shaft of the ultrasound probe and extending distally therefrom beyond the distal end thereof, and a feeler probe tip defined at a distal end of the longitudinal shaft of the tactile feeler probe, the feeler probe tip and the longitudinal shaft of the tactile feeler probe being cooperatively configured and dimensioned to permit the operator to insert the feeler probe tip and the longitudinal shaft of the tactile feeler probe into the pedicle screw pilot hole such that the feeler probe tip is positioned against the selected portion of the side wall of the pedicle screw pilot hole, and to permit the operator to perform thereat a tactile inspection of the selected portion of the side wall of the pedicle screw pilot hole for purposes of detecting manually-detectable cortical breaches located therein;

at least one hollow receiver member mounted with respect to the longitudinal shaft of the ultrasound probe, the at least one hollow receiver member configured and dimensioned to receive a K-wire to permit the instrument to be slidably mounted thereto for purposes of guiding the ultrasound and tactile feeler probes axially relative to the pedicle screw pilot hole; and a first cable assembly for carrying electrical signals to and from the ultrasound transducer in accordance with an ultrasonic imaging mode of use of the instrument, the cable assembly including a proximal end including a first electrical connector for connecting the instrument to a corresponding ultrasound console and current carrying wires extending distally from the electrical connector, through the longitudinal shaft of the ultrasound probe and to the ultrasound transducer;

an ultrasound console including a processor for controlling the medical diagnostic instrument, a display for displaying two-dimensional ultrasonic images obtained therefrom by an operator thereof, and a port for receiving a corresponding cable connector; and a second cable assembly for carrying electrical signals to and from the ultrasound console, the second cable assembly including a second electrical connector coupled to a the port associated with the ultrasound console, a third electrical connector coupled to the first electrical connector, and current carrying wires extending therebetween.

22. A method of exploring a pedicle screw pilot hole formed in the spine of a human patient for cortical breaches located in the axially-extending side-walls thereof, the method including:

presenting a medical diagnostic instrument, the instrument including:

a handle;

an ultrasound probe, the ultrasound probe including a longitudinal shaft extending distally from the handle and terminating in a distal end, and an ultrasound transducer mounted to the longitudinal shaft proximate the distal end thereof, the ultrasound transducer including an array of side-firing ultrasonic energy generation elements extending along the longitudinal shaft;

a tactile feeler probe mounted with respect to the ultrasound probe, the tactile feeler probe including a longitudinal shaft mounted with respect to the longitudinal shaft of the ultrasound probe and extending distally therefrom beyond the distal end thereof, and a feeler probe tip defined at a distal end of the longitudinal shaft of the tactile feeler probe; and at least one hollow receiver member mounted with respect to the longitudinal shaft of the ultrasound probe, the at least one hollow receiver member configured and dimensioned to receive a K-wire to permit the instrument to be slidably mounted thereto for purposes of guiding the ultrasound and tactile feeler probes axially relative to the pedicle screw pilot hole;

mounting and sliding the medical diagnostic instrument along the K-wire to guide the ultrasound and tactile feeler probes axially relative to the pedicle screw pilot hole during a minimally invasive surgical procedure;

employing the handle to manually grasp and manipulate the medical diagnostic instrument relative to the spine of a human patient, including inserting the ultrasound transducer and the distal end of the longitudinal shaft of the ultrasound probe, and the feeler probe tip and the longitudinal shaft of the tactile feeler probe into a pedicle screw pilot hole formed in the spine of the human patient;

positioning the array of side-firing ultrasonic energy generation elements of the ultrasound transducer relative to a selected portion of a side wall of the pedicle screw pilot hole such that the array of side-firing ultrasonic energy generation elements extends axially along, and is positioned against, the selected portion of a side wall of the pedicle screw pilot hole;

employing the array of side-firing ultrasonic energy generation elements of the ultrasound transducer to obtain a two-dimensional image of the selected portion of the side wall for visual inspection for purposes of detecting ultrasonically-detectable cortical breaches located therein;

positioning the feeler probe tip of the tactile feeler probe relative to the selected portion of the side wall of the pedicle screw pilot hole such that the feeler probe tip is positioned against the side wall of the pedicle screw pilot hole;

employing the feeler probe tip of the tactile feeler probe to perform a tactile inspection of the selected portion of the side wall for purposes of detecting manually-detectable cortical breaches located therein; and performing the two positioning and the two employing steps without removing any of the ultrasound transducer or the distal end of the longitudinal shaft of the tactile feeler probe or the feeler probe tip of the longitudinal shaft of the tactile feeler probe from the pedicle screw pilot hole.

\* \* \* \* \*